(12) United States Patent
Nakamura et al.

(10) Patent No.: US 8,618,345 B2
(45) Date of Patent: Dec. 31, 2013

(54) METHOD OF DETOXIFYING A METHYL COMPOUND

(75) Inventors: Koichiro Nakamura, Tokyo (JP); Akihiro Hishinuma, Tokyo (JP); Shinji Kamiya, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 479 days.

(21) Appl. No.: 12/309,992

(22) PCT Filed: Nov. 28, 2007

(86) PCT No.: PCT/JP2007/001312
§ 371 (c)(1),
(2), (4) Date: Apr. 15, 2009

(87) PCT Pub. No.: WO2008/065750
PCT Pub. Date: Jun. 5, 2008

(65) Prior Publication Data
US 2010/0228073 A1 Sep. 9, 2010

(30) Foreign Application Priority Data

Nov. 28, 2006 (JP) ................................ 2006-320300

(51) Int. Cl.
*C01G 28/00* (2006.01)
*C01G 28/02* (2006.01)

(52) U.S. Cl.
USPC .............................. 588/300; 423/87; 423/601

(58) Field of Classification Search
None
See application file for complete search history.

(56) References Cited

U.S. PATENT DOCUMENTS

| | | | | |
|---|---|---|---|---|
| 3,321,537 | A * | 5/1967 | Walker et al. | 570/175 |
| 4,695,447 | A * | 9/1987 | Shultz | 588/314 |
| 5,024,769 | A * | 6/1991 | Gallup | 210/721 |
| 5,458,866 | A * | 10/1995 | Simmons | 423/30 |
| 6,027,543 | A * | 2/2000 | Yoshizaki et al. | 71/11 |
| 7,273,962 | B2 * | 9/2007 | Acey | 588/315 |
| 2008/0145918 | A1 * | 6/2008 | Hishinuma et al. | 435/262.5 |

FOREIGN PATENT DOCUMENTS

| | | | |
|---|---|---|---|
| WO | 2005/100268 | | 10/2005 |
| WO | 2006070885 | * | 6/2006 |
| WO | 2006/070885 | | 7/2006 |

OTHER PUBLICATIONS

Nesmeyanov, A.N. et al. "Alkenyl Derivatives of Arsenic" Institute of Heteroorganic Compounds, Academy of Science USSR, 1199-1203, 1962.*
Parris, G.E., et al. "Reactions Which Relate to the Environmental Mobility of Arsenic and Antimony. I. Quaternization of Trimethylarsine and Trimethylstibine" J. Org. Chem., vol. 40, No. 25 (1975).*
Cullen. W.R., et al. The Reduction of Trimethylarsine Oxide to Trimethylarsine by Thiols: A Mechanistic Model for the Biological Reduction of Arsenicals. Journal of Inorganic Biochemistry 21, 45-60 (1984).*
Bernardo, Martha et al. "One-pot Synthesis of 14 C arsenobetaine bromide" J Label Compd Radiopharm, 47, 393-397 (2004).*
Ismail, Hazar et al. "Preparation of Arsenobetaine hydrobromide" Pertanika 437-439 (1988).*
Kaise, et al., "Cytotoxicological Aspects of Organic Arsenic Compounds Contained in Marine Products Using the Mammalian Cell Culture Technique", Applied Organometallic Chemistry, vol. 12, 137-143 (1998).
Minhas, et al., "Synthesis and Characterization of Arsenobetaine and Arsenocholine Derivatives", Applied Organometallic Chemistry, vol. 12, 635-641 (1998).
Edmonds, et al., "Isolation, Crystal Structure and Synthesis of Arsenobetaine, The Arsenical Constituent of the Western Rock Lobster *Panulirus longipes cygnus* George", Tetrahedron Letters No. 18, 1543-1546, 1977.

* cited by examiner

*Primary Examiner* — Melvin C Mayes
*Assistant Examiner* — Sheng H Davis
(74) *Attorney, Agent, or Firm* — Hamre, Schumann, Mueller & Larson, P.C.

(57) ABSTRACT

It is an object of the present invention to provide a method of detoxifying a methyl compound comprising arsenic etc., effectively and systematically. The method of detoxifying a methyl compound according to the present invention is characterized in that an organic halogenated compound is reacted with a methyl compound comprising at least one element selected from the groups comprising arsenic, antimony and selenium to convert the methyl compound into more harmless substances. Furthermore, in a preferred embodiment of the method of detoxifying a methyl compound according to the present invention, the method is characterized in that the element is arsenic.

14 Claims, 13 Drawing Sheets

METHOD OF DETOXIFYING A METHYL COMPOUND

TECHNICAL FIELD

The present invention relates to a method of converting a methyl compound to a more harmless substance, in particular, a method of converting a methyl compound which is made of at least one selected from the group comprising arsenic, antimony and selenium, to a more harmless substance.

BACKGROUND ART

The metal and metalloid material such as arsenic, antimony and selenium is widely used as an industrial material, for example, semiconductor, but the influence on the organism by being flowed it out into an environment is concerned, since it is a harmful material for the organism.

In the past, as a method for treating these metal and metalloid, a method wherein a flocculating agent such as polychlorinated aluminum (PAC) is added into the wastewater containing an inorganic arsenic such as a harmful arsenous acid, and then the inorganic arsenic is removed by the filtration after the inorganic arsenic is aggregated, adsorbed to the flocculating agent and iron contained in a raw water and then precipitated, or a method of adsorbing an arsenic compound etc. by using an activated alumina, cerium based flocculating agent, are generally known.

On the other hand, it is known in nature that an inorganic arsenic is stored in sea food such as a seaweed, and then a part of the inorganic arsenic is converted to an organic arsenic compound such as dimethyl arsenic by the physiological response (Nonpatent literature 1). And it is generally known that these organic arsenic compound has lower toxicity than that of the inorganic arsenic for the mammal.

Nonpatent literature 1: Kaise et al., 1998, Appl Organomet. Chem., 12 137-143

DISCLOSURE OF THE INVENTION

Problems to be Resolved by the Invention

However, in the above method of removing the metal and metalloid characterized by the use of the filtration and adsorption etc., it is necessary to store or reclaim a polluted sludge containing the harmful compound such as the inorganic arsenic which is still harmful, and an absorbent to which the harmful compound is absorbed, under the condition of sealing off the harmful compound with the use of the concrete etc., in order to prevent it from being leaked to the outside. Therefore, there is a problem that the mass disposal is difficult since a storage place or a large space for a reclaimed area are required.

Furthermore, there remains a problem that even if the inorganic arsenic is accumulated into the see food as mentioned above, only a part of the accumulated inorganic arsenic may be converted to the organic arsenic compound, and harmful inorganic arsenic is still accumulated in the body of the sea food.

Moreover, although the methyl compounds of arsenic etc. are stable and harmless to some extent, if a stable and harmless substance can be obtained conveniently by going a step further, it is desirable from the viewpoint of the environmental protection.

Therefore, it is an object of the present invention to provide a method of detoxifying a methyl compound comprising arsenic etc., effectively and systematically, in order to resolve the above problems.

Means of Solving the Problems

In order to accomplish the above objects, the present inventors made strenuous studies on an alkylation or an arylation of the harmful compounds containing arsenic etc., by an artificial chemical reaction to convert the methyl compound into more stable and harmless substances. As a result, the inventors discovered the present invention.

That is, the method of detoxifying a methyl compound according to the present invention is characterized in that an organic halogenated compound is reacted with a methyl compound comprising at least one element selected from the group comprising arsenic, antimony and selenium to convert the methyl compound into more harmless substances.

Furthermore, in a preferred embodiment of the method of detoxifying a methyl compound according to the present invention, method is characterized in that the methyl compound is at least one of monomethyl compound, dimethyl compound or trimethyl compound.

Furthermore, in a preferred embodiment of the method of detoxifying a methyl compound according to the present invention, the method is characterized in that the element is arsenic.

Furthermore, in a preferred embodiment of the method of detoxifying a methyl compound according to the present invention, the method is characterized in that the organic halogenated compound is alkyl halide.

Furthermore, in a preferred embodiment of the method of detoxifying a methyl compound according to the present invention, the method is characterized in that the alkyl halide is methyl halide.

Furthermore, in a preferred embodiment of the method of detoxifying a methyl compound according to the present invention, the method is characterized in that the methyl halide is at least one selected from the group comprising methyl iodide, methyl bromide or methyl chloride.

Furthermore, in a preferred embodiment of the method of detoxifying a methyl compound according to the present invention, the method is characterized in that the alkyl halide is at least one selected from the group comprising halogenated acetic acid, halogenated alcohol or halogenated ester.

Furthermore, in a preferred embodiment of the method of detoxifying a methyl compound according to the present invention, the method is characterized in that the halogenated acetic acid is at least one selected from the group comprising chloroacetic acid, bromoacetic acid, iodoacetic acid, chloropropionic acid, bromopropionic acid or iodopropionic acid.

Furthermore, in a preferred embodiment of the method of detoxifying a methyl compound according to the present invention, the method is characterized in that the halogenated alcohol is at least one selected from the group comprising chloroethanol, bromoethanol or iodoethanol.

Furthermore, in a preferred embodiment of the method of detoxifying a methyl compound according to the present invention, the method is characterized in that the reaction is further carried out under the existence of the reducing agent capable of reducing at least one selected from the group comprising arsenic, antimony and selenium.

Furthermore, in a preferred embodiment of the method of detoxifying a methyl compound according to the present invention, the method is characterized in that the reducing agent is a material having SH group.

Furthermore, in a preferred embodiment of the method of detoxifying a methyl compound according to the present invention, the method is characterized in that the material having SH group is at least one selected from the group comprising reduced glutathione (GSH), oxidized glutathione, cysteine, S-adenosyl cysteine, sulforaphane or mercaptoalcohol.

Furthermore, in a preferred embodiment of the method of detoxifying a methyl compound according to the present invention, the method is characterized in that the reaction is carried out under the aquatic solvent.

Furthermore, in a preferred embodiment of the method of detoxifying a methyl compound according to the present invention, the method is characterized in that a pH is in the range of 3-10.

Furthermore, in a preferred embodiment of the method of detoxifying a methyl compound according to the present invention, the method is characterized in that the methyl compound is originally from a contaminant, a waste product, industrial products, a hot spring water, a chemical reagent, a chemical weapon, a secondary product of a mine or a smeltery, industrial goods or a natural environment.

Furthermore, in a preferred embodiment of the method of detoxifying a methyl compound according to the present invention, the method is characterized in that the methyl compound is those which the harmful compound containing at least one element selected from the group comprising arsenic, antimony and selenium is methylated.

Furthermore, in a preferred embodiment of the method of detoxifying a methyl compound according to the present invention, the method is characterized in that the mathylation is attained by increasing the oxidation number of a valence of the one element. At this moment, it can thought that the high oxidation number of a valence means higher oxidation number of a valence among the oxidation number which the element can form. For example, in the case of arsenic, it is pentavalent, in the case of antimony, it is pentavalent, in the case of selenium, it is hexavalent etc.

Furthermore, in a preferred embodiment of the method of detoxifying a methyl compound according to the present invention, the method is characterized in that at least one bond of the one element is methylated.

Furthermore, in a preferred embodiment of the method of detoxifying a methyl compound according to the present invention, the method is characterized in that wherein the element is arsenic.

Furthermore, in a preferred embodiment of the method of detoxifying a methyl compound according to the present invention, the method is characterized in that the harmful compound is halogenated, and then the halogenated harmful compound is methylated by the Grignard reaction.

Furthermore, in a preferred embodiment of the method of detoxifying a methyl compound according to the present invention, the method is characterized in that the harmful compound is selected from the groups comprising arsenious acid, arsenic pentoxide, arsenic trichloride, arsenic pentachloride, arsenic sulfide compound, cyano arsenic compound, chloro arsenic compound, and other arsenic inorganic salt.

Effect of Invention

The method of detoxifying a methyl compound according to the present invention has an advantageous effect that it is possible to produce the method of converting the methyl compound made of arsenic etc., into more harmless substances effectively and systematically.

BEST MODE FOR CARRYING OUT THE INVENTION

Figure 1:
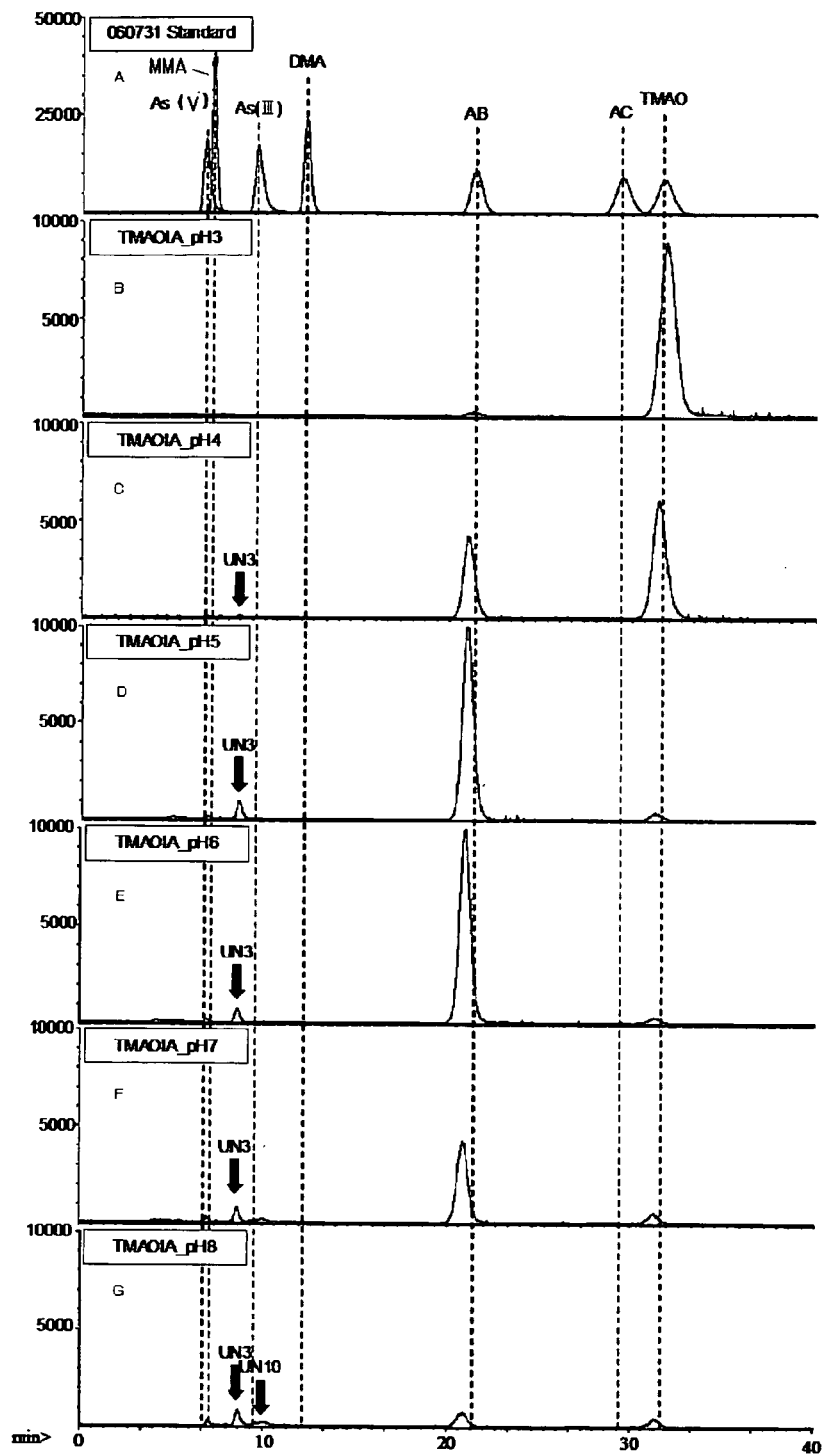
FIG. 1 gives a HPLC-ICP-MS chromatograph in the case with the reaction for 4 hours in the Example 1.

Detailed descriptions of the present invention are explained as follows. The method of detoxifying the methyl compound according to the present invention is characterized in that an organic halogenated compound is reacted with the methyl compound comprising at least one element selected from the group comprising arsenic, antimony and selenium to convert the methyl compound into more harmless substances. The methyl compound is not particularly limited as long as it comprises arsenic, antimony, selenium etc. Further, the methyl compound is not particularly limited, but includes for example monomethyl compound, dimethyl compound, or trimethyl compound etc.

Furthermore, the derivation of the methyl compound is also not particularly limited. For example, the derivation of the methyl compound can be recited as those which is originally from a contaminant, a waste product, industrial products, a hot spring water, a chemical reagent, a chemical weapon, a secondary product of a mine or a smeltery, industrial goods or a natural environment. Although the methyl compound can be prepared synthetically from bacteria or in a liver of animals, such as rat, the present invention is also intended for those obtained in this way, is not particularly limited to any origins. After all, the derivation is not particularly limited as long as it is the methyl compound.

Although the methyl compound includes those which is reduced their toxicity by the so-called methylation of the inorganic arsenic etc., said inorganic arsenic etc., exists as the harmful compound on the ground. The term "the harmful compound" used herein means a compound which gives any adverse affect to the organism when it is flowed out into the environment and exposed to the organism.

As the harmful compound containing arsenic among the above harmful compound, mention may be made of arsenious acid, arsenic pentoxide, arsenic trichloride, arsenic pentachloride, arsenic sulfide compound, cyano arsenic compound, chloro arsenic compound, and other arsenic inorganic salt and or the like. In these arsenic, for example, $LD_{50}$ (mg/kg) (50% of the fatal dose in mouse) is less or equal to 20, and therefore, it is generally a poisonous value for the organism.

Further, as a harmful compound containing antimony, mention may be made of antimony trioxide, antimony pentoxide, antimony trichloride, and antimony pentachloride or the like.

Further, as a harmful compound containing selenium, mention may be made of selenium dioxide, selenium trioxide. Needless to say, the objections to be detoxified in the present invention also includes the methyl compounds which is originally from the harmful compounds as mentioned above. The method of detoxify the harmful compound containing at least one element selected from the group comprising arsenic, antimony and selenium will be hereinafter explained.

In the present invention, the organic halogenated compounds react with the above methyl compounds (which contain monomethyl compounds, dimethyl compounds or trimethyl compounds etc.) to convert the methyl compounds to more harmless substances. As to the monomethyl compounds, for example, as the monomethyl compounds made of arsenic mention may be made of monomethyl arsinic acid etc., moreover, as the monomethyl compounds made of antimony mention may be made of monomethyl antimony etc., as the monomethyl compounds made of selenium mention may be made of monomethyl selenol etc. Furthermore, as to the dimethyl compounds, for example, as the dimethyl compounds made of arsenic mention may be made of dimethyl arsonic acid, dimethyl arsinoyl acetate, dimethyl arsinoyl ethanol etc., further, as dimethyl compounds made of antimony mention may be made of dimethyl antimony etc., further as dimethyl compounds made of selenium mention may be made of dimethyl selenide (dimethyl selenide) etc. As to the trimethyl compounds, for example, as the trimethyl compounds comprising arsenic mention may be made of trimethylarsineoxide, trimethylarsine, and as the trimethyl compounds comprising antimony mention may be made of trimethylantimony, trimethylantimonydihydroxide, trimethylantimonydichloride etc., and as the trimethyl compounds comprising selenium mention may be made of trimethylselenium etc.

Furthermore, the organic halogenated compound is not particularly limited, but to obtain the desired harmless substances, may be recited as alkyl halide, halogenated acetic acid, or halogenated alcohol etc.

As the alkyl halide, for example, mention may be made of methyl halide such as methyl iodide, methyl bromide, methyl chloride. Such alkyl halide may be use in the case that the objective of the invention intends to make it more harmless conclusively by obtaining a tetramethyl compound.

Further, as the halogenated acetic acid, mention may be made of chloroacetic acid, bromoacetic acid, iodoacetic acid, chloropropionic acid, bromopropionic acid, iodopropionic acid or the like. The use of these halogenated acetic acid such as iodoacetic acid makes it possible to obtain more harmless arsenobetaine etc., if it reacts with trimethylarsineoxide.

Further, as the halogenated alcohol, mention may be made of chloroethanol, bromoethanol, iodoethanol or the like. The use of these halogenated alcohol makes it possible to obtain more harmless arsenocholine etc., if it reacts with trimethylarsineoxide.

Especially, it is desirable to convert the methyl compound into more harmless arsenocholine or arsenobetaine in the case of the detoxification of the methyl compound made of arsenic because arsenocholine and arsenobetaine are stable substances which do not tend to take place the demethylation or degradation under the ordinary circumstances. In particular, the toxicity of arsenobetaine is approximately $1/300$ and therefore it is lower compared with that of inorganic arsenic (arsenic trioxide). From the 1980s, arsenobetaine is evaluated as a harmless arsenic compound internationally. Based on this perspective, it is thought that it is desirable to attain the detoxification by obtaining arsenobetaine conclusively.

At this moment, the stability of arsenobetaine as an example will be explained. From the viewpoint of a half life of a substance in the body (BHT), the half life of arsenobetaine is 3.5 hours while, the half life of inorganic arsenic is 28 hours, and those of the monomethyl compound (MMA) and dimethyl compound (DMA) are 5-6 hours. Therefore, from the viewpoint of a half life, it is especially recognized that the safety of arsenobetaine to the living organism is high. Furthermore, it is recognized that arsenobetaine is stable since it makes no demethylation if it is accumulated in the body.

In a method of detoxifying a methyl compound according to the present invention, further the reaction may be carried out under the existence of the reducing agent capable of reducing at least one selected from the group comprising arsenic, antimony and selenium. The existence of such reducing agent may make it possible to further accelerate the reaction of the detoxification. Although it is thought that a reducing ability for the arsenic or the transmethylation reaction are likely to be a rate controlling in the conversion to the arsenobetaine, it is thought that the conversion of arsenic to the arsenobetaine etc., may be accelerated by adding those substances. As the reducing agent like this, for example, a material having the SH group may be mentioned, which may be specifically at least one selected from the groups comprising reduced glutathione (GSH), oxidized glutathione, cysteine, S-adenosyl cysteine, sulforaphane, mercaptoethanol.

As to the reaction solvent, although the organic solvent such as toluene, diethyl ether can be used, in the present invention, it is possible to carry out the reaction under water type of solvent at a less expensive without the use of the organic solvent which a careful handling is generally required.

Furthermore, in a viewpoint that it is possible to attain more stabilization and detoxification of more methyl compounds, it is desirable that a pH of the reaction solution is in a range of 3-10. In a viewpoint that it is possible to obtain a desired detoxified substance for more short time, a pH is in a range of 4-8, more preferably, a pH is in a range of 4-6.

A temperature of the reaction is not particularly limited, but may also be a room temperature. In a viewpoint that a mixed solvent of a water and the organic solvent may be used, as a temperature of the reaction, it may be carried out at 5-250° C. Furthermore, a reaction time is also not particularly limited.

As explained above, according to the method of the present invention, it is possible to convert the methyl compound into more harmless substance under the mild condition in extremely safe, to attain the cost reduction because of the use of the water type of the solvent.

In the method of the detoxification according to the present invention, the harmful compounds are collected from a contaminant, a waste product, industrial products, a hot spring water, a chemical reagent, a chemical weapon, a secondary product of a mine or a smeltery, industrial goods or a natural environment, to detoxify the obtained harmful compounds by converting them to methyl compound, the method of the present invention makes it possible to further attain the detoxification and stabilization of the obtained methyl compounds.

More specifically, for example, it is possible to apply in several treatment such as a treatment of the groundwater such as the contaminated groundwater which has emerged as a social issue (India, Bangladesh, China, Chile etc.), a treatment of a raw material gas of the gallium arsenic semiconductor (arsine), a treatment of a clarifying agent of the liquid crystal substrate glass (arsenic trioxide), a treatment of an arsenic containing water etc., originally from a CCA (copper-chromated-arsenic) containing waste wood material. That is, since the contaminated groundwater, the raw material gas, the clarifying agent and the arsenic containing water etc., as mentioned above are made of so-called harmful compound containing arsenic etc., if those harmful compounds are collected, conclusively the method of detoxifying the methyl compound of the present invention makes it possible to convert them to more harmless and stable substance at high-efficiency and by using more safer system.

As mentioned above, as the methyl compound, it is possible to use those which the harmful compound containing at least one element selected from the groups comprising arsenic, antimony and selenium is methylated. Such methyl compound will be explained as follows.

In a preferred embodiment of the method of the detoxification according to the present invention, the methyl compound is those which the harmful compound containing at least one element selected from the groups comprising arsenic, antimony and selenium is methylated (those detoxified by the methylation). At this moment, as mentioned above, the term "the harmful compound" used herein means a compound which gives any adverse affect to the organism when it is flowed out into the environment and exposed to the organism.

In particular, in the viewpoint that the 50% of an inhibition of cell growth concentration ($IC_{50}$) or the 50% of a lethal dose ($LD_{50}$) is greater, and therefore it is possible to attain more detoxification, the methylation of the harmful compound is preferably attained by increasing the oxidation number of a valence of the one element contained in the above harmful compound. Specifically, it is possible to increase the oxidation number of a valence of the one element by the methylation as described above. Moreover, it is preferable to convert a trivalent of the oxidation number of a valence to a pentavalent in the case that the element is arsenic or antimony, and it is preferable to convert a tetravalent of the oxidation number of a valence to a hexavalent in the case of selenium.

At this moment, it is preferable to methylate at least one bond of the one element contained in the above harmful compound. Specifically, it is possible to methlate at least one bond of the one element by carrying out the substitution reaction or the addition reaction with the use of methyl halide or the Grignard reagent In a further preferred embodiment of the method of the detoxification according to the present invention, in a viewpoint that it is possible easily to obtain a methylating reagent, it is preferable to halogenate the above harmful compound, and to methylate the halogenated harmful compound by the Grignard reaction.

The halogenation of the harmful compound, for example, may be carried out by reacting the harmful compound with the halogen gas under the existence of sulfur, or reacting the harmful compound with hydrohalic acid, or reacting the harmful compound with an alkyl-metal halide such as potassium iodide under the existence of acid such as hydrochloric acid.

The Grignard reaction of the halogenated harmful compound may be carried out by reacting the halogenated harmful compound with the Grignard reagent. At this moment, in the method of the detoxification according to the present invention, the Grignard reagent as used may be shown in the following chemical formula 1:

$$RMgX \qquad \text{Chemical formula 1}$$

(wherein R=methyl group). It is possible to add the methyl group to the one element of the harmful compound by using such Grignard reagent. Such Grignard reagent may be synthesized from the reaction of appropriate organic halide and metal magnesium according to the conventional method.

In a viewpoint that it is easy to obtain the methylation reagent, the methyl group is small and therefore, it is easy to bond the one element of the harmful compound, a biocompatibility is high in a view of the preventive medicine, it is preferable to methylate the harmful compound, to convert the harmful compound into monomethyl compound, dimethyl compound or trimethyl compound. Moreover, in a viewpoint that the $LD_{50}$ can be improved and more detoxified compound can be obtained, the harmful compound is preferably converted to trimethyl compound.

It is possible to further detoxify the methyl compound obtained thus such as monomethyl compound, dimethyl compound or trimethyl compound by reacting the methyl compound with the organic halide compound as mentioned before according to the method of detoxifying the methyl compound of the present invention.

EXAMPLE

The present invention will be concretely explained in more detail with reference to Examples, but the invention is not intended to be interpreted as being limited to Examples.

Example 1

20 μL of 1 ppm trimethylarsineoxide (TMAO) and 50 μL of 100 mM glutathione reduced form (GSH) and 135 μL of 7.4 μM iodoacetic acid were mixed. The concentrations of TMAO, GSH and iodoacetic acid existing in the solution after mixing are 0.2 µM, 5 mM, and 1 mM, respectively. 205 µL of the mixture were reacted in 795 µL of 100 mM phosphoric acid-citrate buffer solution (pH 3, 4, 5, 6, 7, 8) at 37° C., an amount of the arsenic compound about TMAO and arsenobetaine (AB) existing in the mixture after the reaction was analyzed at the HPLC-ICP-MS. The HPLC-ICP-MS chromatograms are shown in FIGS. 1-4 (FIG. 1: 4 hours of the reaction time, FIG. 2: 24 hours of the reaction time, FIG. 3: 100 hours of the reaction time, FIG. 4: 439 hours of the reaction time, A: standard sample, B: pH 3, C: pH 4, D: pH 5, E: pH 6, F: pH 7, G: pH 8). The concentration of each samples were assayed for quantitative value by comparing a dimension of a peak attributed to TMAO and AB with a dimension of the standard sample having a predetermined concentration as to the chromatograms of FIGS. 1-4. Table 1 shows an amount of the concentration of the arsenic compound in the mixture after the reaction, the FIG. 5 shows a graphic representation of the table 1. In FIG. 5, a vertical axis shows the concentration of arsenic (ng/mL), a horizontal axis shows the reaction time.

TABLE 1

Figure 2:
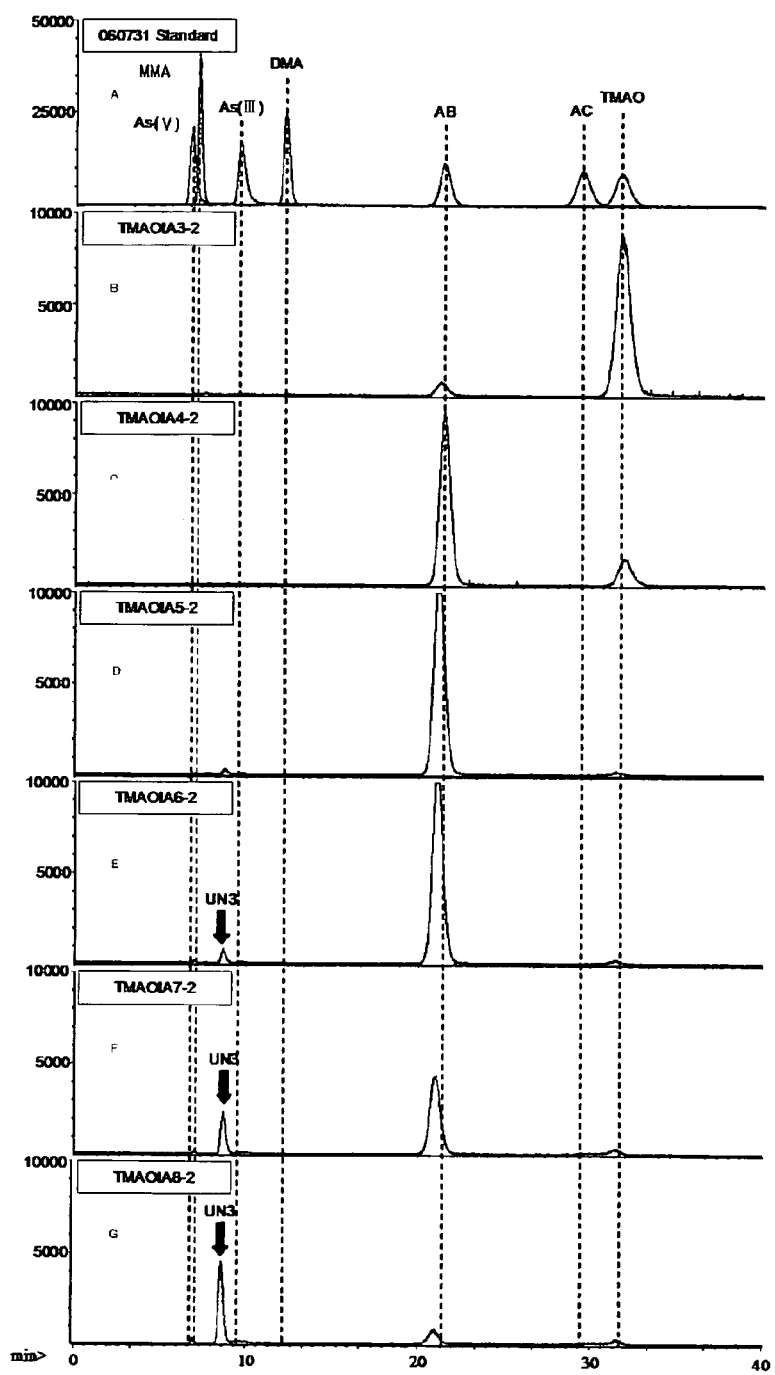
FIG. 2 gives a HPLC-ICP-MS chromatograph in the case with the reaction for 24 hours in the Example 1.
Figure 3:
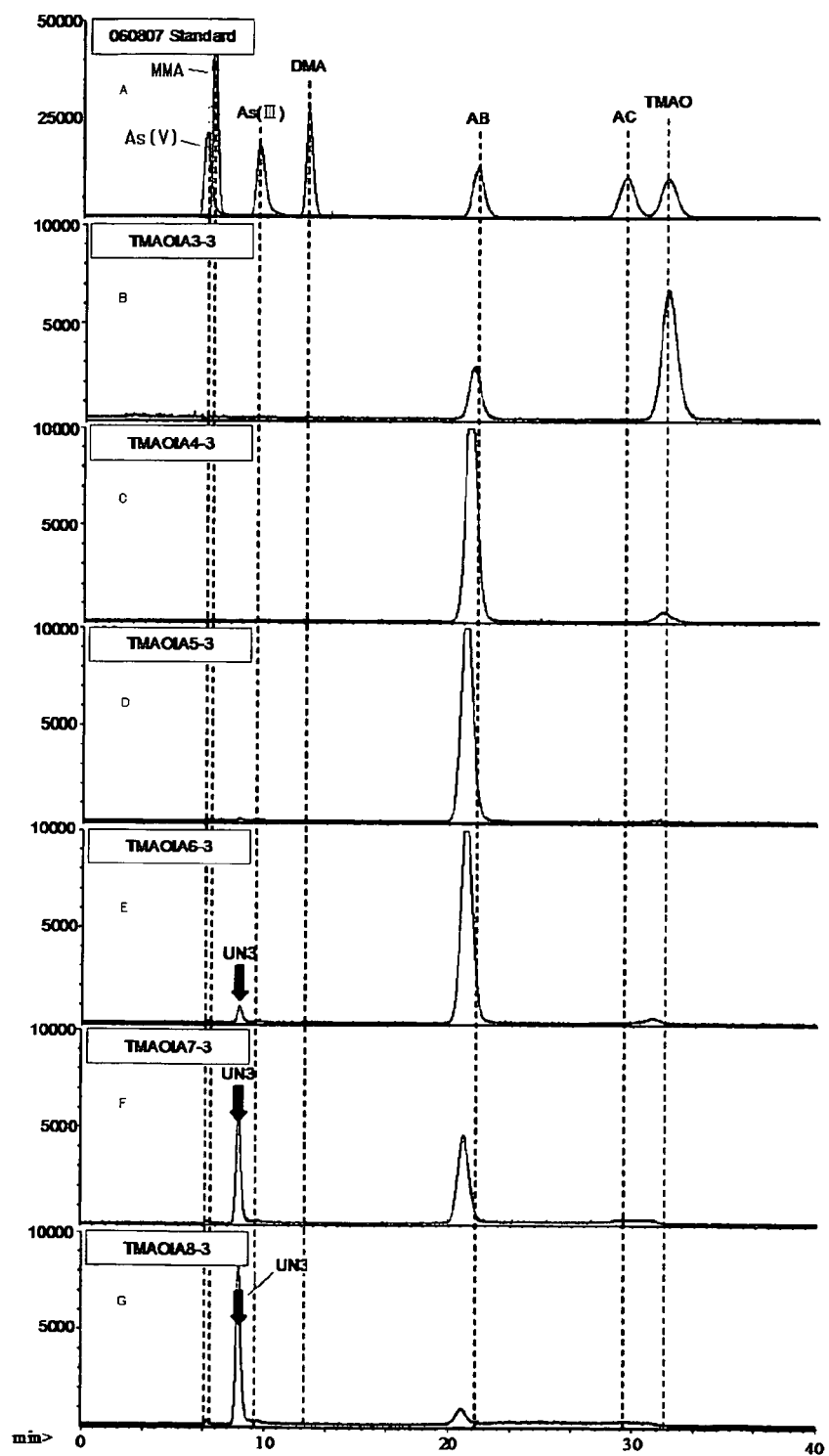
FIG. 3 gives a HPLC-ICP-MS chromatograph in the case with the reaction for 100 hours in the Example 1.
Figure 4:
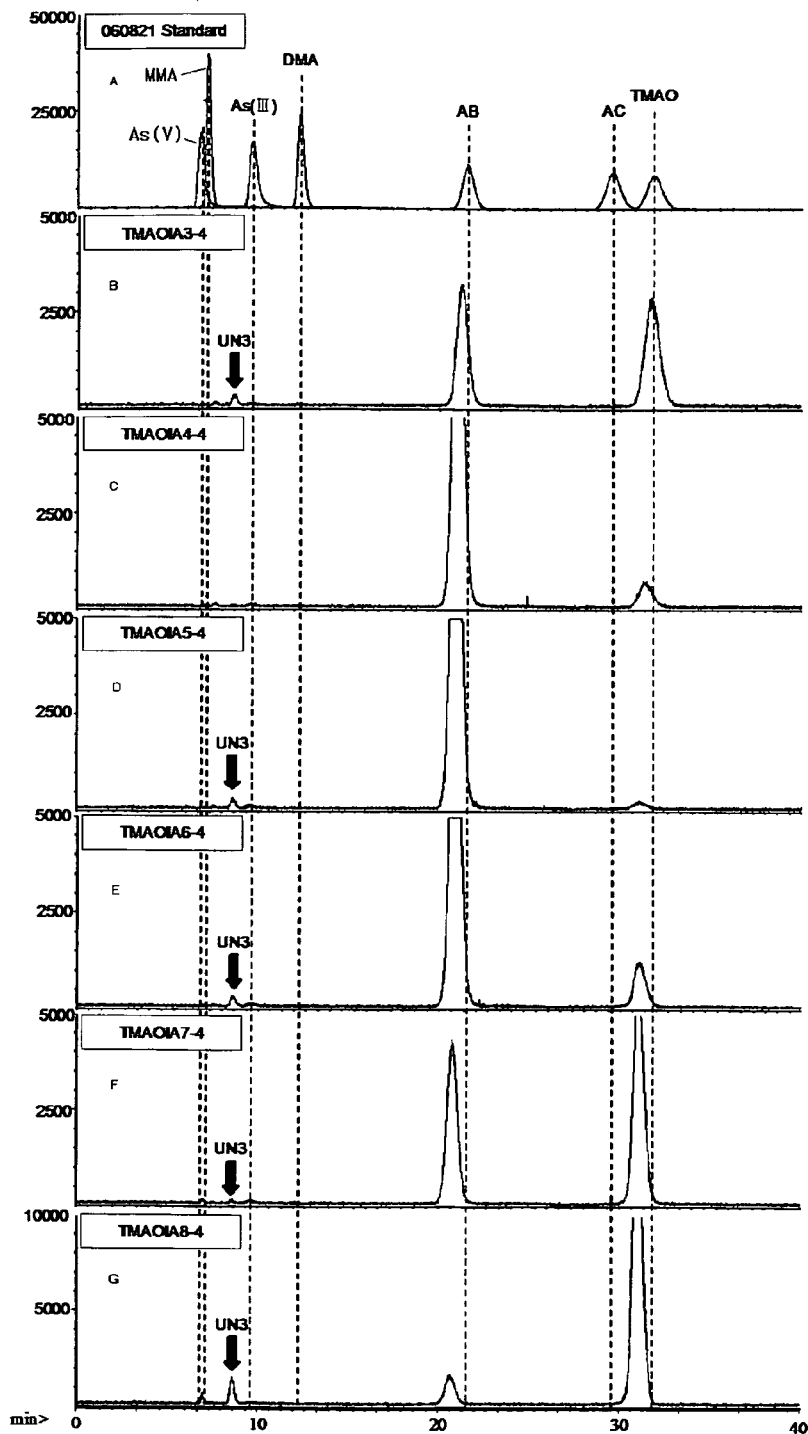
FIG. 4 gives a HPLC-ICP-MS chromatograph in the case with the reaction for 439 hours in the Example 1.
Figure 5:
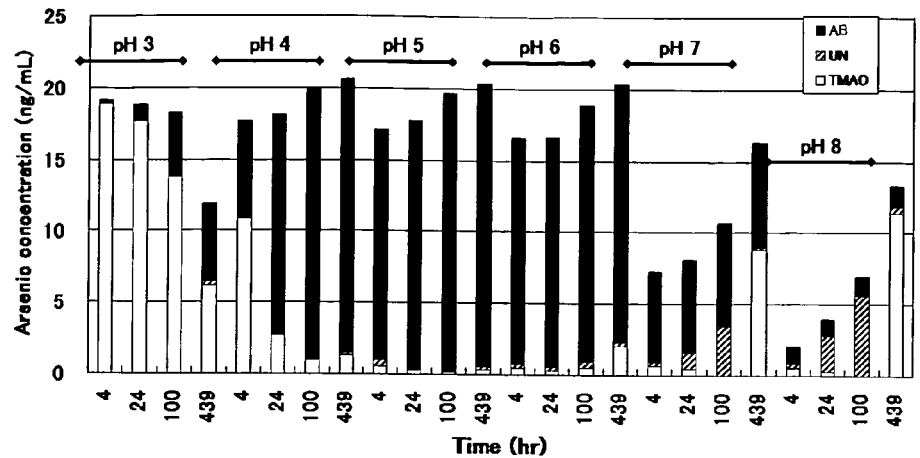
FIG. 5 gives the concentration of the arsenic compound existing in the mixed solution in various sort of pH and the time of reaction after the reaction in the Example 1.

| Sample | pH | Time (hr) | Concentration (ng As/mL) | | | | remarks |
|---|---|---|---|---|---|---|---|
| | | | TMAO | UN | AB | Total | |
| TMAOIA3-1 | 3 | 4 | 18.88 | 0.00 | 0.28 | 19.16 | FIG. 1-B |
| TMAOIA3-2 | 3 | 24 | 17.68 | 0.00 | 1.17 | 18.85 | FIG. 2-B |
| TMAOIA3-3 | 3 | 100 | 13.82 | 0.00 | 4.46 | 18.28 | FIG. 3-B |
| TMAOIA3-4 | 3 | 439 | 6.19 | 0.24 | 5.53 | 11.96 | FIG. 4-B |
| TMAOIA4-1 | 4 | 4 | 10.87 | 0.00 | 6.81 | 17.68 | FIG. 1-C |
| TMAOIA4-2 | 4 | 24 | 2.70 | 0.00 | 15.41 | 18.11 | FIG. 2-C |
| TMAOIA4-3 | 4 | 100 | 1.01 | 0.00 | 18.86 | 19.87 | FIG. 3-C |
| TMAOIA4-4 | 4 | 439 | 1.30 | 0.12 | 19.17 | 20.59 | FIG. 4-C |
| TMAOIA5-1 | 5 | 4 | 0.57 | 0.40 | 16.13 | 17.10 | FIG. 1-D |
| TMAOIA5-2 | 5 | 24 | 0.27 | 0.00 | 17.44 | 17.71 | FIG. 2-D |
| TMAOIA5-3 | 5 | 100 | 0.10 | 0.00 | 19.55 | 19.65 | FIG. 3-D |
| TMAOIA5-4 | 5 | 439 | 0.33 | 0.23 | 19.82 | 20.38 | FIG. 4-D |
| TMAOIA6-1 | 6 | 4 | 0.46 | 0.30 | 15.83 | 16.59 | FIG. 1-E |
| TMAOIA6-2 | 6 | 24 | 0.29 | 0.24 | 16.18 | 16.71 | FIG. 2-E |
| TMAOIA6-3 | 6 | 100 | 0.47 | 0.44 | 17.98 | 18.89 | FIG. 3-E |
| TMAOIA6-4 | 6 | 439 | 2.06 | 0.24 | 18.09 | 20.39 | FIG. 4-E |
| TMAOIA7-1 | 7 | 4 | 0.68 | 0.26 | 6.35 | 7.29 | FIG. 1-F |
| TMAOIA7-2 | 7 | 24 | 0.42 | 1.19 | 6.48 | 8.09 | FIG. 2-F |
| TMAOIA7-3 | 7 | 100 | 0.00 | 3.46 | 7.20 | 10.66 | FIG. 3-F |
| TMAOIA7-4 | 7 | 439 | 8.81 | 0.10 | 7.43 | 16.34 | FIG. 4-F |
| TMAOIA8-1 | 8 | 4 | 0.55 | 0.31 | 1.18 | 2.04 | FIG. 1-G |
| TMAOIA8-2 | 8 | 24 | 0.30 | 2.49 | 1.16 | 3.95 | FIG. 2-G |
| TMAOIA8-3 | 8 | 100 | 0.00 | 5.62 | 1.34 | 6.96 | FIG. 3-G |
| TMAOIA8-4 | 8 | 439 | 11.38 | 0.51 | 1.44 | 13.33 | FIG. 4-G |

Figure 6:
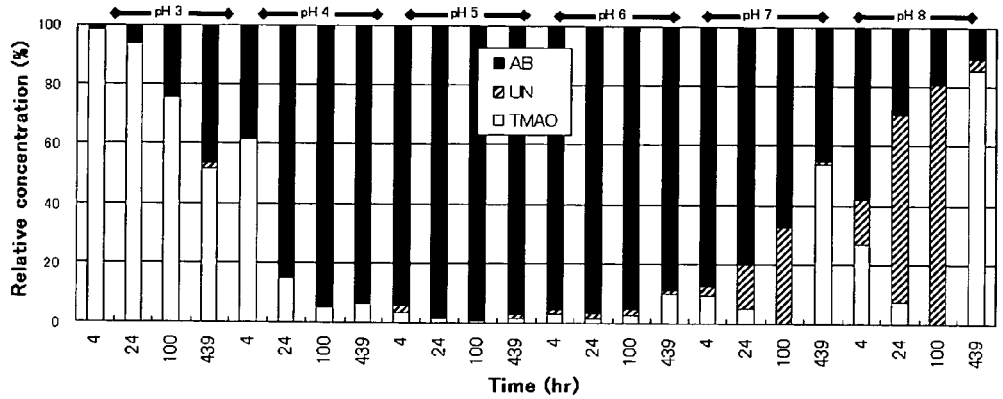
FIG. 6 gives the relative concentration (percentage) of the arsenic compound existing in the mixed solution in various sort of pH and the time of reaction after the reaction in the Example 1.

As it is clear from the table 1, it is recognized that TMAO is converted to more harmless and stable arsenobetaine by reacting it with an organic halide compound (iodoacetic acid). Moreover, the "UN" described in table 1 and FIG. 5 shows unknown compounds. Hereinafter, it is the same in the following tables and figures. Furthermore, the result calculated on percentage of the relative concentration as to the concentration of the arsenic compound of the table 1 is shown in table 2 and FIG. 6. In FIG. 6, a vertical axis shows the relative concentration (%), a horizontal axis shows the reaction time.

TABLE 2

| Sample | pH | Time (hr) | Relative concentration (%) | | | | remarks |
|---|---|---|---|---|---|---|---|
| | | | TMAO | UN | AB | Total | |
| TMAOIA3-1 | 3 | 4 | 98.5 | 0.0 | 1.5 | 100.0 | FIG. 1-B |
| TMAOIA3-2 | 3 | 24 | 93.8 | 0.0 | 6.2 | 100.0 | FIG. 2-B |
| TMAOIA3-3 | 3 | 100 | 75.6 | 0.0 | 24.4 | 100.0 | FIG. 3-B |
| TMAOIA3-4 | 3 | 439 | 51.8 | 2.0 | 46.2 | 100.0 | FIG. 4-B |
| TMAOIA4-1 | 4 | 4 | 61.5 | 0.0 | 38.5 | 100.0 | FIG. 1-C |
| TMAOIA4-2 | 4 | 24 | 14.9 | 0.0 | 85.1 | 100.0 | FIG. 2-C |
| TMAOIA4-3 | 4 | 100 | 5.1 | 0.0 | 94.9 | 100.0 | FIG. 3-C |
| TMAOIA4-4 | 4 | 439 | 6.3 | 0.6 | 93.1 | 100.0 | FIG. 4-C |
| TMAOIA5-1 | 5 | 4 | 3.3 | 2.3 | 94.3 | 100.0 | FIG. 1-D |
| TMAOIA5-2 | 5 | 24 | 1.5 | 0.0 | 98.5 | 100.0 | FIG. 2-D |
| TMAOIA5-3 | 5 | 100 | 0.5 | 0.0 | 99.5 | 100.0 | FIG. 3-D |
| TMAOIA5-4 | 5 | 439 | 1.6 | 1.1 | 97.3 | 100.0 | FIG. 4-D |
| TMAOIA6-1 | 6 | 4 | 2.8 | 1.8 | 95.4 | 100.0 | FIG. 1-E |
| TMAOIA6-2 | 6 | 24 | 1.7 | 1.4 | 96.8 | 100.0 | FIG. 2-E |
| TMAOIA6-3 | 6 | 100 | 2.5 | 2.3 | 95.2 | 100.0 | FIG. 3-E |
| TMAOIA6-4 | 6 | 439 | 10.1 | 1.2 | 88.7 | 100.0 | FIG. 4-E |
| TMAOIA7-1 | 7 | 4 | 9.3 | 3.6 | 87.1 | 100.0 | FIG. 1-F |
| TMAOIA7-2 | 7 | 24 | 5.2 | 14.7 | 80.1 | 100.0 | FIG. 2-F |
| TMAOIA7-3 | 7 | 100 | 0.0 | 32.5 | 67.5 | 100.0 | FIG. 3-F |
| TMAOIA7-4 | 7 | 439 | 53.9 | 0.6 | 45.5 | 100.0 | FIG. 4-F |
| TMAOIA8-1 | 8 | 4 | 27.0 | 15.2 | 57.8 | 100.0 | FIG. 1-G |
| TMAOIA8-2 | 8 | 24 | 7.6 | 63.0 | 29.4 | 100.0 | FIG. 2-G |
| TMAOIA8-3 | 8 | 100 | 0.0 | 80.7 | 19.3 | 100.0 | FIG. 3-G |
| TMAOIA8-4 | 8 | 439 | 85.4 | 3.8 | 10.8 | 100.0 | FIG. 4-G |

Arsenobetaine (AB) was produced in each pH. In particular, AB was produced in high concentrations at pH 4-6.

Example 2

Next, the detoxification of trimethyl compound will be explained. The detoxification of the trimethyl compound was examined in the same manner as in Example 1, except that cysteine (Cys) was used instead of glutathione reduced form (GSH). In the Example 2, the experimental tests at 50° C. and 80° C. were also carried out in addition to those of at 37° C. of the reaction temperature.

Figure 7:
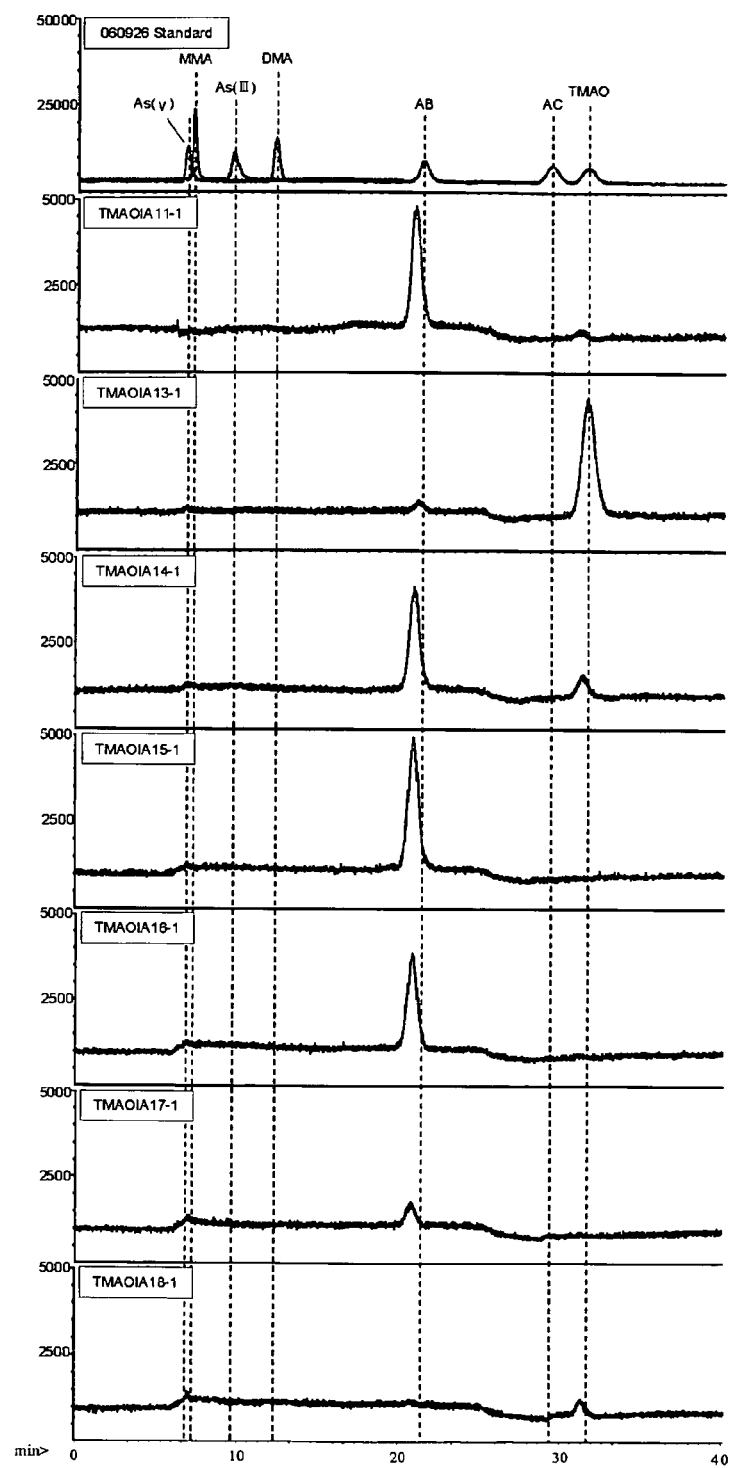
FIG. 7 gives a HPLC-ICP-MS chromatograph in the case with the reaction at 37° C. for 4 hours in the Example 2.
Figure 8:
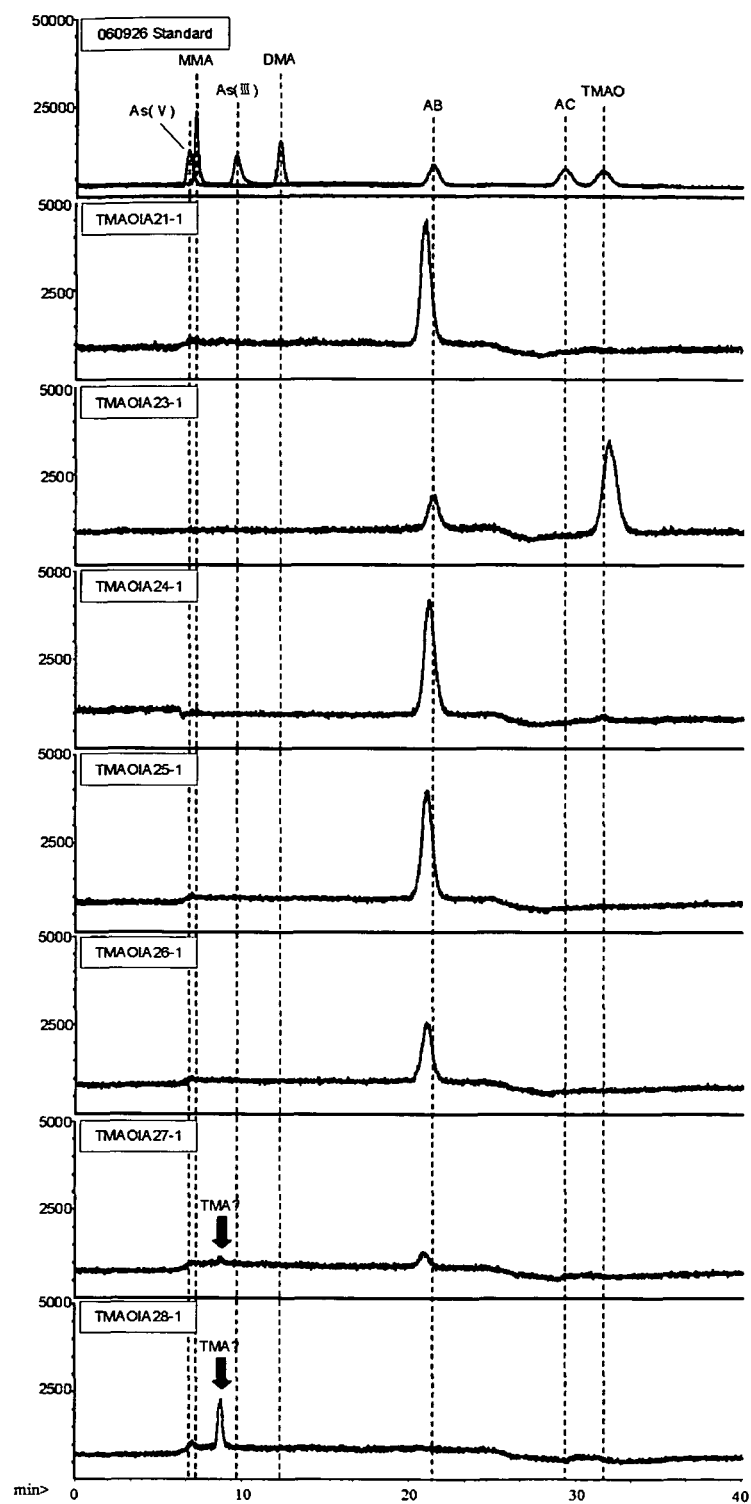
FIG. 8 gives a HPLC-ICP-MS chromatograph in the case with the reaction at 50° C. for 4 hours in the Example 2.
Figure 9:
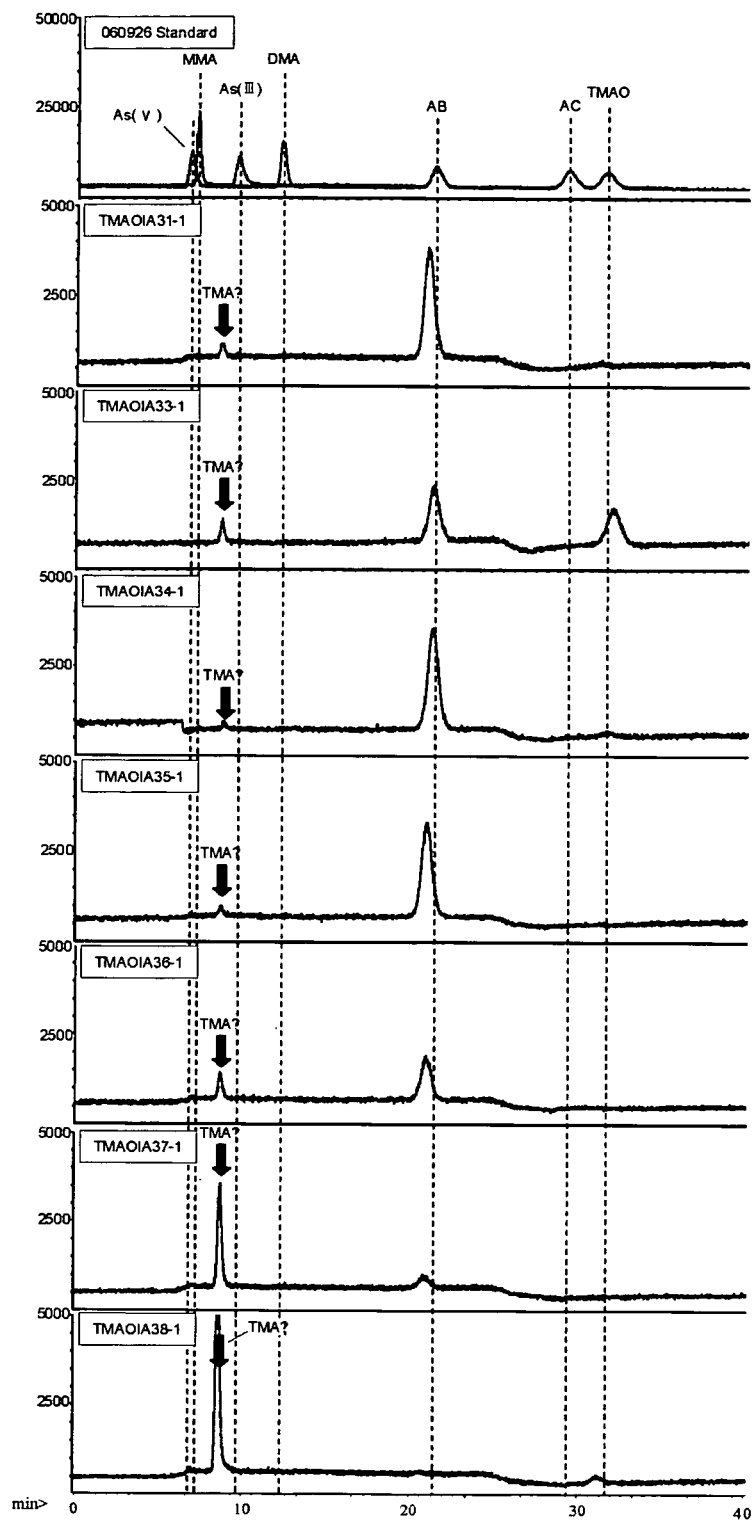
FIG. 9 gives a HPLC-ICP-MS chromatograph in the case with the reaction at 80° C. for 4 hours in the Example 2.
Figure 10:
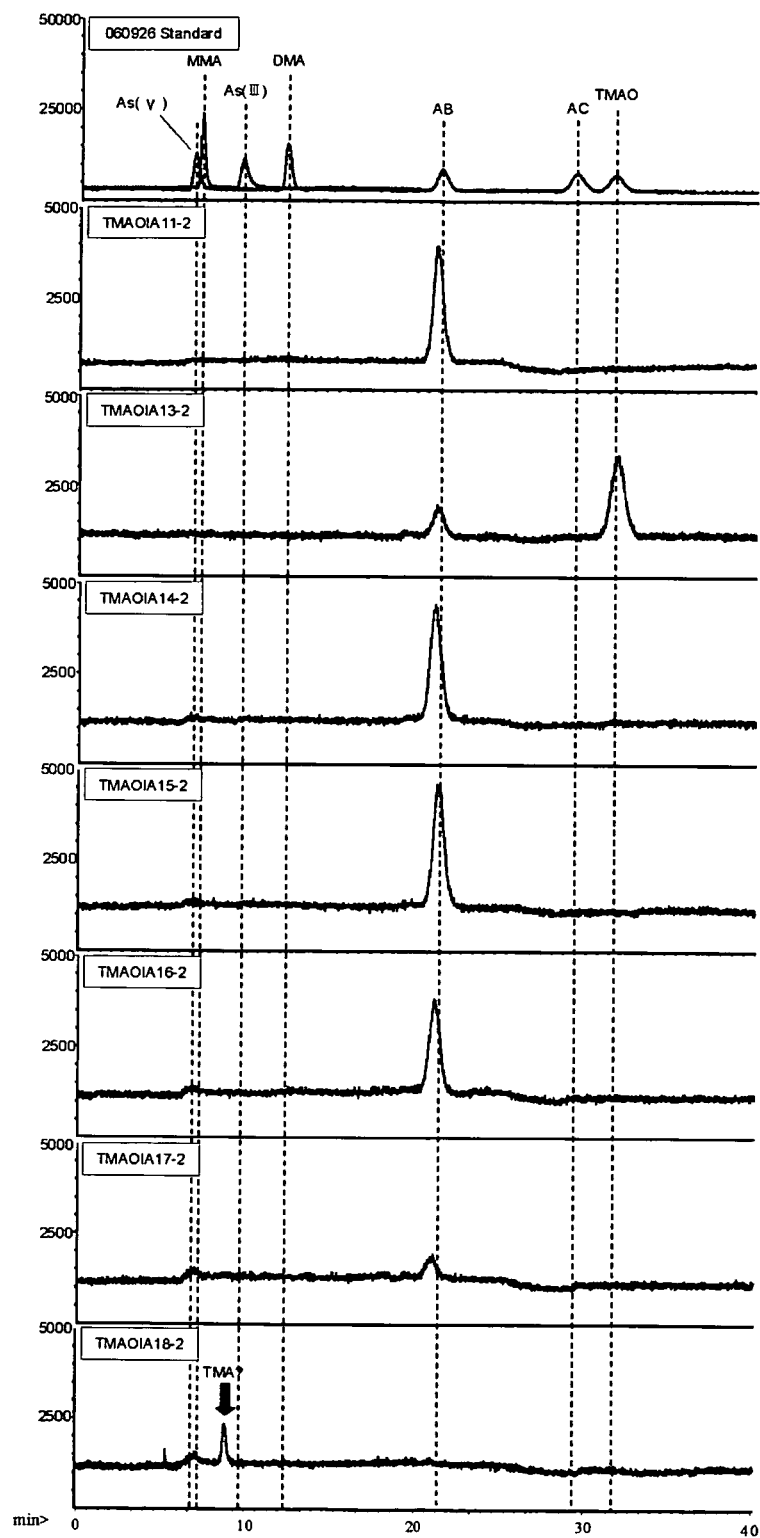
FIG. 10 gives a HPLC-ICP-MS chromatograph in the case with the reaction at 37° C. for 24 hours in the Example 2.
Figure 11:
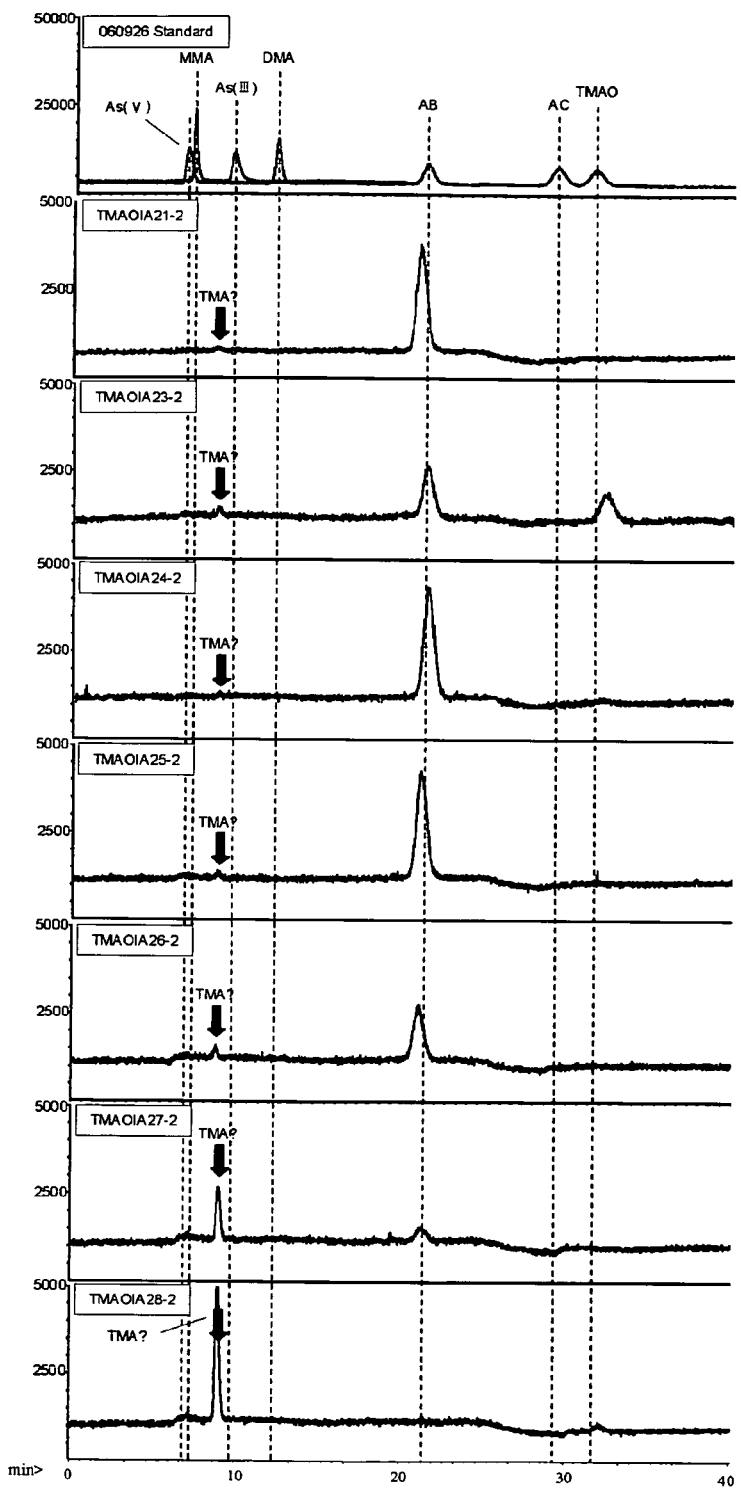
FIG. 11 gives a HPLC-ICP-MS chromatograph in the case with the reaction at 50° C. for 24 hours in the Example 2.
Figure 12:
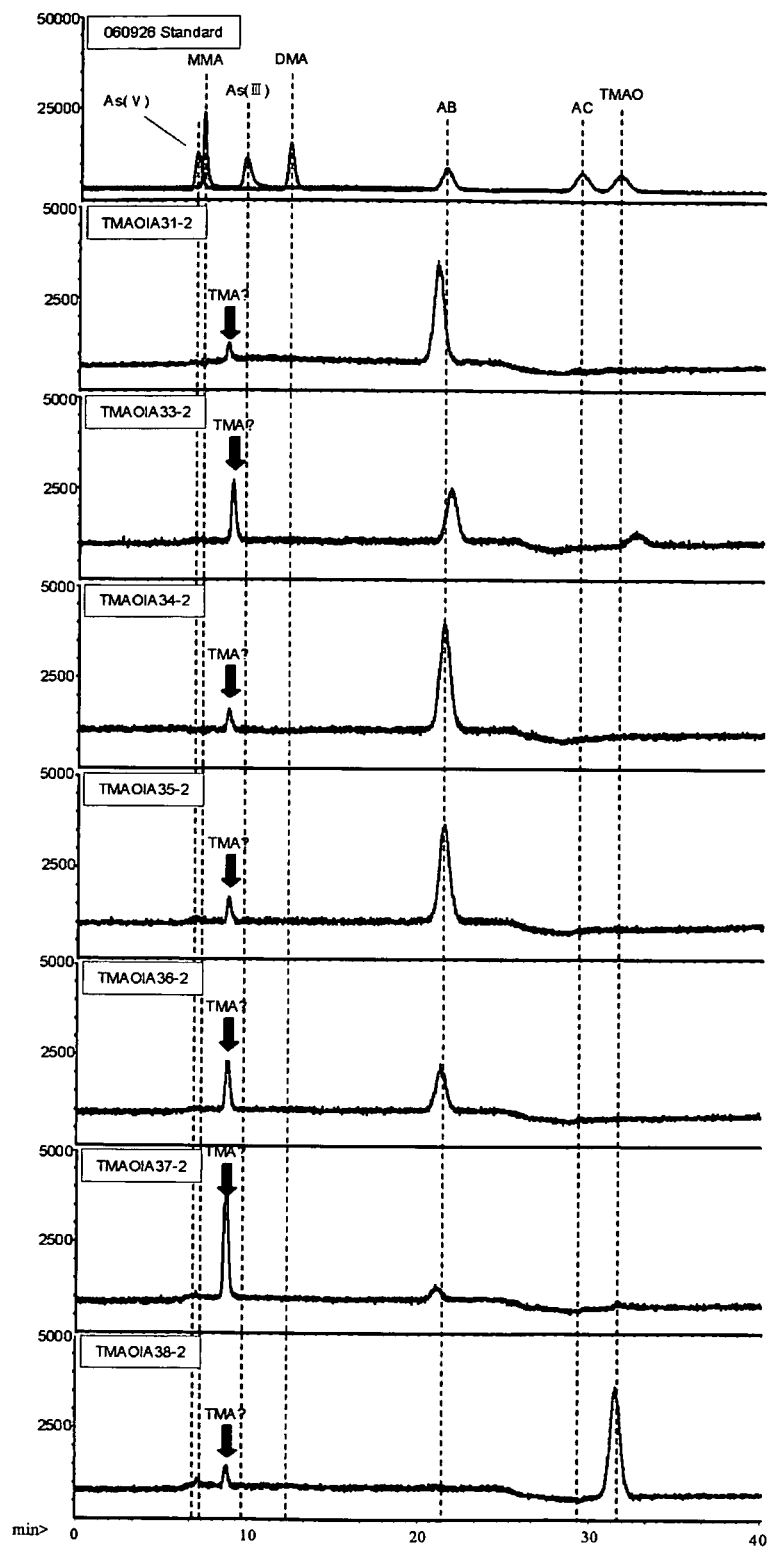
FIG. 12 gives a HPLC-ICP-MS chromatograph in the case with the reaction at 80° C. for 24 hours in the Example 2.
Figure 13:
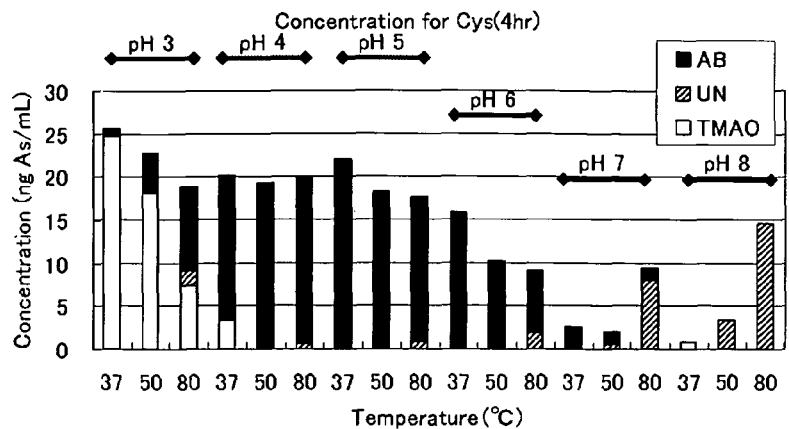
FIG. 13 gives the concentration of the arsenic compound existing in the mixed solution after the reaction in various sort of pH and the time of reaction after the reaction in the Example 2.
Figure 14:
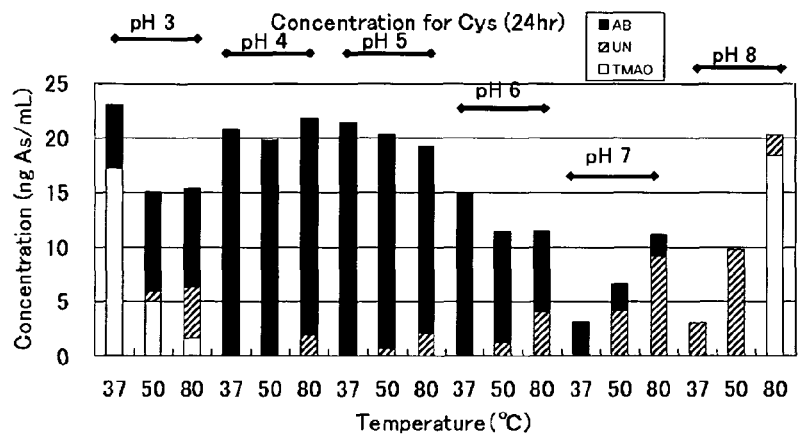
FIG. 14 gives the concentration of the arsenic compound existing in the mixed solution after the reaction in various sort of pH and the time of the reaction after the reaction in the Example 2.

The HPLC-ICP-MS chromatograms are shown in FIGS. 7-12 (FIG. 7: 4 hours of the reaction time, 37° C. of the reaction temperature, FIG. 8: 4 hours of the reaction time, 50° C. of the reaction temperature, FIG. 9: 4 hours of the reaction time, 80° C. of the reaction temperature, FIG. 10: 24 hours of the reaction time, 37° C. of the reaction temperature, FIG. 11: 24 hours of the reaction time, 50° C. of the reaction temperature, FIG. 12: 24 hours of the reaction time, 80° C. of the reaction temperature). The concentrations of TMAO and AB were assayed by the chromatogram in the same manner as in Example 1. The table 3 shows the concentration of the arsenic compound existing in the mixture after the reaction, FIGS. 13 and 14 show a graphic representation of the table 3. In FIGS. 13 and 14, a vertical axis shows the concentration of the arsenic compound (ng/mL), a horizontal axis shows the reaction temperature (° C.).

TABLE 3

| Sample | reducing agent | pH | reaction tem. (° C.) | reaction time (h) | reaction tem. (° C.) | Concentration (ng As/mL) TMAO | UN | AB | Total | remarks |
|---|---|---|---|---|---|---|---|---|---|---|
| TMAOIA11-1 | GSH | 5 | 37 | 4 | 37 | 0.00 | 0.00 | 19.44 | 19.44 | FIG. 7-B |
| TMAOIA21-1 | GSH | 5 | 50 | 4 | 50 | 0.00 | 0.00 | 19.45 | 19.45 | FIG. 8-B |
| TMAOIA31-1 | GSH | 5 | 80 | 4 | 80 | 0.00 | 1.29 | 18.68 | 19.97 | FIG. 9-B |
| TMAOIA11-2 | GSH | 5 | 37 | 24 | 37 | 0.00 | 0.00 | 21.98 | 21.98 | FIG. 10-B |
| TMAOIA21-2 | GSH | 5 | 50 | 24 | 50 | 0.00 | 0.45 | 20.44 | 20.89 | FIG. 11-B |
| TMAOIA31-2 | GSH | 5 | 80 | 24 | 80 | 0.00 | 1.65 | 19.25 | 20.90 | FIG. 12-B |
| TMAOIA13-1 | Cys | 3 | 37 | 4 | 37 | 24.69 | 0.00 | 1.01 | 25.70 | FIG. 7-C |
| TMAOIA23-1 | Cys | 3 | 50 | 4 | 50 | 18.15 | 0.00 | 4.67 | 22.82 | FIG. 8-C |
| TMAOIA33-1 | Cys | 3 | 80 | 4 | 80 | 7.32 | 1.87 | 9.61 | 18.80 | FIG. 9-C |
| TMAOIA14-1 | Cys | 4 | 37 | 4 | 37 | 3.43 | 0.00 | 16.74 | 20.17 | FIG. 7-D |
| TMAOIA24-1 | Cys | 4 | 50 | 4 | 50 | 0.00 | 0.00 | 19.20 | 19.20 | FIG. 8-D |
| TMAOIA34-1 | Cys | 4 | 80 | 4 | 80 | 0.00 | 0.68 | 19.18 | 19.86 | FIG. 9-D |
| TMAOIA15-1 | Cys | 5 | 37 | 4 | 37 | 0.00 | 0.00 | 21.99 | 21.99 | FIG. 7-E |
| TMAOIA25-1 | Cys | 5 | 50 | 4 | 50 | 0.00 | 0.00 | 18.25 | 18.25 | FIG. 8-E |
| TMAOIA35-1 | Cys | 5 | 80 | 4 | 80 | 0.00 | 0.87 | 16.75 | 17.62 | FIG. 9-E |
| TMAOIA16-1 | Cys | 6 | 37 | 4 | 37 | 0.00 | 0.00 | 15.80 | 15.80 | FIG. 7-F |
| TMAOIA26-1 | Cys | 6 | 50 | 4 | 50 | 0.00 | 0.00 | 10.23 | 10.23 | FIG. 8-F |
| TMAOIA36-1 | Cys | 6 | 80 | 4 | 80 | 0.00 | 1.97 | 7.13 | 9.10 | FIG. 9-F |
| TMAOIA17-1 | Cys | 7 | 37 | 4 | 37 | 0.00 | 0.00 | 2.60 | 2.60 | FIG. 7-G |
| TMAOIA27-1 | Cys | 7 | 50 | 4 | 50 | 0.00 | 0.61 | 1.41 | 2.02 | FIG. 8-G |
| TMAOIA37-1 | Cys | 7 | 80 | 4 | 80 | 0.00 | 8.06 | 1.36 | 9.42 | FIG. 9-G |
| TMAOIA18-1 | Cys | 8 | 37 | 4 | 37 | 0.81 | 0.00 | 0.00 | 0.81 | FIG. 7-H |
| TMAOIA28-1 | Cys | 8 | 50 | 4 | 50 | 0.00 | 3.39 | 0.00 | 3.39 | FIG. 8-H |
| TMAOIA38-1 | Cys | 8 | 80 | 4 | 80 | 14.56 | 0.00 | 0.00 | 14.56 | FIG. 9-H |
| TMAOIA13-2 | Cys | 3 | 37 | 24 | 37 | 17.23 | 0.00 | 5.83 | 23.06 | FIG. 10-C |
| TMAOIA23-2 | Cys | 3 | 50 | 24 | 50 | 5.05 | 0.86 | 9.15 | 15.06 | FIG. 11-C |
| TMAOIA33-2 | Cys | 3 | 80 | 24 | 80 | 1.66 | 4.67 | 9.04 | 15.37 | FIG. 12-C |
| TMAOIA14-2 | Cys | 4 | 37 | 24 | 37 | 0.00 | 0.00 | 20.79 | 20.79 | FIG. 10-D |
| TMAOIA24-2 | Cys | 4 | 50 | 24 | 50 | 0.00 | 0.00 | 19.82 | 19.82 | FIG. 11-D |
| TMAOIA34-2 | Cys | 4 | 80 | 24 | 80 | 0.00 | 1.93 | 19.83 | 21.76 | FIG. 12-D |
| TMAOIA15-2 | Cys | 5 | 37 | 24 | 37 | 0.00 | 0.00 | 21.36 | 21.36 | FIG. 10-E |
| TMAOIA25-2 | Cys | 5 | 50 | 24 | 50 | 0.00 | 0.67 | 19.66 | 20.33 | FIG. 11-E |
| TMAOIA35-2 | Cys | 5 | 80 | 24 | 80 | 0.00 | 2.11 | 17.14 | 19.25 | FIG. 12-E |
| TMAOIA16-2 | Cys | 6 | 37 | 24 | 37 | 0.00 | 0.00 | 14.95 | 14.95 | FIG. 10-F |
| TMAOIA26-2 | Cys | 6 | 50 | 24 | 50 | 0.00 | 1.28 | 10.14 | 11.42 | FIG. 11-F |
| TMAOIA36-2 | Cys | 6 | 80 | 24 | 80 | 0.00 | 4.14 | 7.28 | 11.42 | FIG. 12-F |
| TMAOIA17-2 | Cys | 7 | 37 | 24 | 37 | 0.00 | 0.00 | 3.16 | 3.16 | FIG. 10-G |
| TMAOIA27-2 | Cys | 7 | 50 | 24 | 50 | 0.00 | 4.16 | 2.47 | 6.63 | FIG. 11-G |
| TMAOIA37-2 | Cys | 7 | 80 | 24 | 80 | 0.00 | 9.19 | 2.08 | 11.27 | FIG. 12-G |
| TMAOIA18-2 | Cys | 8 | 37 | 24 | 37 | 0.00 | 3.06 | 0.00 | 3.06 | FIG. 10-H |
| TMAOIA28-2 | Cys | 8 | 50 | 24 | 50 | 0.00 | 9.80 | 0.00 | 9.80 | FIG. 11-H |
| TMAOIA38-2 | Cys | 8 | 80 | 24 | 80 | 18.43 | 1.92 | 0.00 | 20.35 | FIG. 12-H |

Figure 15:
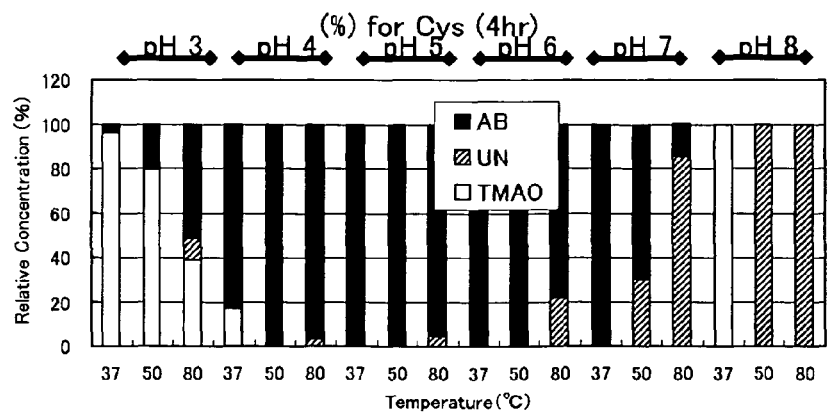
FIG. 15 gives the relative concentration (percentage) of the arsenic compound existing in the mixed solution after the reaction in various sort of pH and the time of reaction in the case of the reaction for 4 hours in the Example 2.
Figure 16:
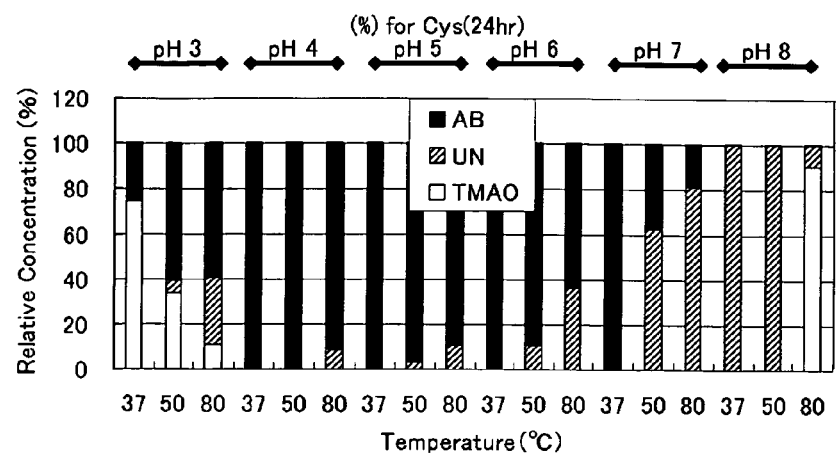
FIG. 16 gives the relative concentration (percentage) of the arsenic compound existing the mixed solution after the reaction in various sort of pH and the time of reaction in the case of the reaction for 24 hours in the Example 2.

FIG. 13 shows the concentration of the arsenic compound at each pHs in the case of 4 hours of the reaction time, and FIG. 14 shows the concentration of the arsenic compound in the case of 24 hours of the reaction time. Furthermore, the results calculated on percentage of the relative concentration as to the concentration of those arsenic compound are shown in table 4, FIG. 15 and FIG. 16. In FIGS. 15 and 16, a vertical axis shows the relative concentration (%) of the arsenic compound, a horizontal axis shows the reaction temperature (° C.).

TABLE 4

| Sample | reducing agent | pH | reaction temp. (° C.) | reaction time (h) | reaction temp. (° C.) | Relative Concentration (%) TMAO | UN | AB | Total | remarks |
|---|---|---|---|---|---|---|---|---|---|---|
| TMAOIA11-1 | GSH | 5 | 37 | 4 | 37 | 0 | 0 | 100 | 100 | FIG. 7-B |
| TMAOIA21-1 | GSH | 5 | 50 | 4 | 50 | 0 | 0 | 100 | 100 | FIG. 8-B |
| TMAOIA31-1 | GSH | 5 | 80 | 4 | 80 | 0 | 6 | 94 | 100 | FIG. 9-B |
| TMAOIA11-2 | GSH | 5 | 37 | 24 | 37 | 0 | 0 | 100 | 100 | FIG. 10-B |
| TMAOIA21-2 | GSH | 5 | 50 | 24 | 50 | 0 | 2 | 98 | 100 | FIG. 11-B |
| TMAOIA31-2 | GSH | 5 | 80 | 24 | 80 | 0 | 8 | 92 | 100 | FIG. 12-B |
| TMAOIA13-1 | Cys | 3 | 37 | 4 | 37 | 96 | 0 | 4 | 100 | FIG. 7-C |
| TMAOIA23-1 | Cys | 3 | 50 | 4 | 50 | 80 | 0 | 20 | 100 | FIG. 8-C |
| TMAOIA33-1 | Cys | 3 | 80 | 4 | 80 | 39 | 10 | 51 | 100 | FIG. 9-C |
| TMAOIA14-1 | Cys | 4 | 37 | 4 | 37 | 17 | 0 | 83 | 100 | FIG. 7-D |
| TMAOIA24-1 | Cys | 4 | 50 | 4 | 50 | 0 | 0 | 100 | 100 | FIG. 8-D |
| TMAOIA34-1 | Cys | 4 | 80 | 4 | 80 | 0 | 3 | 97 | 100 | FIG. 9-D |
| TMAOIA15-1 | Cys | 5 | 37 | 4 | 37 | 0 | 0 | 100 | 100 | FIG. 7-E |
| TMAOIA25-1 | Cys | 5 | 50 | 4 | 50 | 0 | 0 | 100 | 100 | FIG. 8-E |
| TMAOIA35-1 | Cys | 5 | 80 | 4 | 80 | 0 | 5 | 95 | 100 | FIG. 9-E |
| TMAOIA16-1 | Cys | 6 | 37 | 4 | 37 | 0 | 0 | 100 | 100 | FIG. 7-F |

TABLE 4-continued

| Sample | reducing agent | pH | reaction temp. (° C.) | reaction time (h) | reaction temp. (° C.) | Relative Concentration (%) TMAO | UN | AB | Total | remarks |
|---|---|---|---|---|---|---|---|---|---|---|
| TMAOIA26-1 | Cys | 6 | 50 | 4 | 50 | 0 | 0 | 100 | 100 | FIG. 8-F |
| TMAOIA36-1 | Cys | 6 | 80 | 4 | 80 | 0 | 22 | 78 | 100 | FIG. 9-F |
| TMAOIA17-1 | Cys | 7 | 37 | 4 | 37 | 0 | 0 | 100 | 100 | FIG. 7-G |
| TMAOIA27-1 | Cys | 7 | 50 | 4 | 50 | 0 | 30 | 70 | 100 | FIG. 8-G |
| TMAOIA37-1 | Cys | 7 | 80 | 4 | 80 | 0 | 86 | 14 | 100 | FIG. 9-G |
| TMAOIA18-1 | Cys | 8 | 37 | 4 | 37 | 100 | 0 | 0 | 100 | FIG. 7-H |
| TMAOIA28-1 | Cys | 8 | 50 | 4 | 50 | 0 | 100 | 0 | 100 | FIG. 8-H |
| TMAOIA38-1 | Cys | 8 | 80 | 4 | 80 | 0 | 100 | 0 | 100 | FIG. 9-H |
| TMAOIA13-2 | Cys | 3 | 37 | 24 | 37 | 75 | 0 | 25 | 100 | FIG. 10-C |
| TMAOIA23-2 | Cys | 3 | 50 | 24 | 50 | 34 | 6 | 61 | 100 | FIG. 11-C |
| TMAOIA33-2 | Cys | 3 | 80 | 24 | 80 | 11 | 30 | 59 | 100 | FIG. 12-C |
| TMAOIA14-2 | Cys | 4 | 37 | 24 | 37 | 0 | 0 | 100 | 100 | FIG. 10-D |
| TMAOIA24-2 | Cys | 4 | 50 | 24 | 50 | 0 | 0 | 100 | 100 | FIG. 11-D |
| TMAOIA34-2 | Cys | 4 | 80 | 24 | 80 | 0 | 9 | 91 | 100 | FIG. 12-D |
| TMAOIA15-2 | Cys | 5 | 37 | 24 | 37 | 0 | 0 | 100 | 100 | FIG. 10-E |
| TMAOIA25-2 | Cys | 5 | 50 | 24 | 50 | 0 | 3 | 97 | 100 | FIG. 11-E |
| TMAOIA35-2 | Cys | 5 | 80 | 24 | 80 | 0 | 11 | 89 | 100 | FIG. 12-E |
| TMAOIA16-2 | Cys | 6 | 37 | 24 | 37 | 0 | 0 | 100 | 100 | FIG. 10-F |
| TMAOIA26-2 | Cys | 6 | 50 | 24 | 50 | 0 | 11 | 89 | 100 | FIG. 11-F |
| TMAOIA36-2 | Cys | 6 | 80 | 24 | 80 | 0 | 36 | 64 | 100 | FIG. 12-F |
| TMAOIA17-2 | Cys | 7 | 37 | 24 | 37 | 0 | 0 | 100 | 100 | FIG. 10-G |
| TMAOIA27-2 | Cys | 7 | 50 | 24 | 50 | 0 | 63 | 37 | 100 | FIG. 11-G |
| TMAOIA37-2 | Cys | 7 | 80 | 24 | 80 | 0 | 82 | 18 | 100 | FIG. 12-G |
| TMAOIA18-2 | Cys | 8 | 37 | 24 | 37 | 0 | 100 | 0 | 100 | FIG. 10-H |
| TMAOIA28-2 | Cys | 8 | 50 | 24 | 50 | 0 | 100 | 0 | 100 | FIG. 11-H |
| TMAOIA38-2 | Cys | 8 | 80 | 24 | 80 | 91 | 9 | 0 | 100 | FIG. 12-H |

FIG. 15 shows the relative concentration of the arsenic compound at each pHs in the case of 4 hours of the reaction time, and FIG. 16 shows the relative concentration of the arsenic compound in the case of 24 hours of the reaction time. As a result of these, the production of arsenobetaine was confirmed even if cysteine was used.

Example 3

Next, the detoxification of the trimethyl compound is explained. The detoxification of the trimethyl compound was examined in the same manner as in Example 1, except that glutathione reduced form (GSH) or cysteine were used as the reducing agent and ethyl iodoacetate was used as the organic halide compound. The reaction temperatures are 37° C., 50° C., and 80° C., respectively, and the reaction times are 4 hours, 16 hours and 54 hours. The reaction path is as follows.

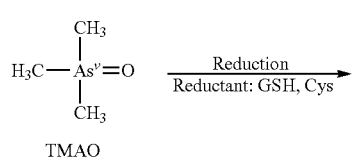

TMAO

[Chemical 1]

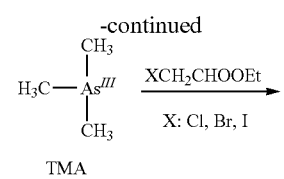

TMA

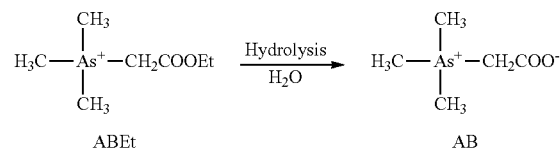

ABEt     AB

The amount of production of the arsenic compounds existing in the mixture after the reaction was analyzed by HPLC-ICP-MS. The results of analysis are shown in table 5. Moreover, in the following tables and figures, it is shown that TMAO: trimethylarsineoxide, TMA: trimethylarsine, ABEt: arsenobetaine ethyl ester, AB: arsenobetaine.

TABLE 5

| | conditions of reaction | | | | concentration of As com. (ng As/mL) | | | | |
|---|---|---|---|---|---|---|---|---|---|
| sample | reducing agent | pH | reaction tem. (° C.) | reaction time (h) | TMAO | TMA | ABEt | AB | Total |
| TMAOIA41-1 | GSH | 5 | 37 | 4 | 6.5 | 0.2 | 8.0 | 0.0 | 14.7 |
| TMAOIA43-1 | Cys | 3 | 37 | 4 | 14.7 | 0.1 | 3.1 | 0.0 | 17.9 |
| TMAOIA44-1 | Cys | 4 | 37 | 4 | 4.2 | 0.1 | 11.6 | 0.0 | 15.9 |
| TMAOIA45-1 | Cys | 5 | 37 | 4 | 4.1 | 0.4 | 8.7 | 0.2 | 13.3 |

TABLE 5-continued

| | conditions of reaction | | | | concentration of As com. (ng As/mL) | | | | |
|---|---|---|---|---|---|---|---|---|---|
| sample | reducing agent | pH | reaction tem. (° C.) | reaction time (h) | TMAO | TMA | ABEt | AB | Total |
| TMAOIA46-1 | Cys | 6 | 37 | 4 | 8.0 | 0.7 | 1.5 | 0.2 | 10.4 |
| TMAOIA47-1 | Cys | 7 | 37 | 4 | 0.6 | 0.1 | 0.0 | 0.0 | 0.7 |
| TMAOIA48-1 | Cys | 8 | 37 | 4 | 1.0 | 0.2 | 0.0 | 0.0 | 1.2 |
| TMAOIA51-1 | GSH | 5 | 50 | 4 | 0.0 | 0.0 | 0.0 | 0.0 | 0.0 |
| TMAOIA53-1 | Cys | 3 | 50 | 4 | 1.8 | 0.0 | 0.7 | 0.0 | 2.6 |
| TMAOIA54-1 | Cys | 4 | 50 | 4 | 0.0 | 0.0 | 0.4 | 0.0 | 0.4 |
| TMAOIA55-1 | Cys | 5 | 50 | 4 | 0.0 | 0.1 | 0.0 | 0.0 | 0.1 |
| TMAOIA56-1 | Cys | 6 | 50 | 4 | 0.0 | 0.0 | 0.0 | 0.0 | 0.0 |
| TMAOIA57-1 | Cys | 7 | 50 | 4 | 0.0 | 0.0 | 0.0 | 0.0 | 0.0 |
| TMAOIA58-1 | Cys | 8 | 50 | 4 | 0.0 | 0.1 | 0.0 | 0.0 | 0.1 |
| TMAOIA61-1 | GSH | 5 | 80 | 4 | 0.0 | 0.0 | 0.0 | 0.0 | 0.0 |
| TMAOIA63-1 | Cys | 3 | 80 | 4 | 1.2 | 0.1 | 0.9 | 0.0 | 2.1 |
| TMAOIA64-1 | Cys | 4 | 80 | 4 | 0.3 | 0.1 | 2.2 | 0.2 | 2.7 |
| TMAOIA65-1 | Cys | 5 | 80 | 4 | 0.8 | 0.8 | 1.3 | 0.4 | 3.3 |
| TMAOIA66-1 | Cys | 6 | 80 | 4 | 0.4 | 1.3 | 0.0 | 0.3 | 2.0 |
| TMAOIA67-1 | Cys | 7 | 80 | 4 | 0.0 | 0.4 | 0.0 | 0.0 | 0.4 |
| TMAOIA68-1 | Cys | 8 | 80 | 4 | 0.5 | 1.5 | 0.0 | 0.0 | 2.0 |
| TMAOIA41-2 | GSH | 5 | 37 | 54 | 3.0 | 0.1 | 9.9 | 1.9 | 14.9 |
| TMAOIA43-2 | Cys | 3 | 37 | 54 | 12.9 | 0.1 | 6.0 | 0.5 | 19.5 |
| TMAOIA44-2 | Cys | 4 | 37 | 54 | 0.4 | 0.4 | 15.4 | 1.4 | 17.6 |
| TMAOIA45-2 | Cys | 5 | 37 | 54 | 3.2 | 0.1 | 9.6 | 2.1 | 15.1 |
| TMAOIA46-2 | Cys | 6 | 37 | 54 | 17.1 | 0.0 | 1.1 | 1.7 | 20.0 |
| TMAOIA47-2 | Cys | 7 | 37 | 54 | 21.2 | 0.0 | 0.0 | 0.3 | 21.5 |
| TMAOIA48-2 | Cys | 8 | 37 | 54 | 19.7 | 0.0 | 0.0 | 0.0 | 19.7 |
| TMAOIA51-2 | GSH | 5 | 50 | 16 | 1.1 | 0.0 | 6.9 | 1.9 | 9.9 |
| TMAOIA53-2 | Cys | 3 | 50 | 16 | 6.6 | 0.1 | 6.5 | 0.7 | 13.9 |
| TMAOIA54-2 | Cys | 4 | 50 | 16 | 1.2 | 0.0 | 11.8 | 1.3 | 14.3 |
| TMAOIA55-2 | Cys | 5 | 50 | 16 | 6.9 | 0.1 | 5.5 | 1.8 | 14.3 |
| TMAOIA56-2 | Cys | 6 | 50 | 16 | 11.2 | 0.2 | 0.5 | 1.1 | 13.0 |
| TMAOIA57-2 | Cys | 7 | 50 | 16 | 8.8 | 0.0 | 0.0 | 0.2 | 9.0 |
| TMAOIA58-2 | Cys | 8 | 50 | 16 | 12.1 | 0.0 | 0.0 | 0.0 | 12.1 |
| TMAOIA61-2 | GSH | 5 | 80 | 16 | 4.9 | 0.1 | 2.2 | 5.1 | 12.2 |
| TMAOIA63-2 | Cys | 3 | 80 | 16 | 1.9 | 6.7 | 6.2 | 2.0 | 16.8 |
| TMAOIA64-2 | Cys | 4 | 80 | 16 | 1.7 | 0.6 | 8.5 | 4.4 | 15.2 |
| TMAOIA65-2 | Cys | 5 | 80 | 16 | 0.4 | 5.0 | 1.4 | 4.5 | 11.3 |
| TMAOIA66-2 | Cys | 6 | 80 | 16 | 10.7 | 0.2 | 0.0 | 1.3 | 12.2 |
| TMAOIA67-2 | Cys | 7 | 80 | 16 | 12.6 | 0.0 | 0.0 | 0.2 | 12.9 |
| TMAOIA68-2 | Cys | 8 | 80 | 16 | 18.1 | 0.0 | 0.0 | 0.0 | 18.1 |

TABLE 6

| | conditions of reaction | | | | relative concentration (%) | | | | |
|---|---|---|---|---|---|---|---|---|---|
| sample | reducing agent | pH | reaction tem. (° C.) | reaction time (h) | TMAO | TMA | ABEt | AB | Total |
| TMAOIA41-1 | GSH | 5 | 37 | 4 | 44 | 2 | 54 | 0 | 100 |
| TMAOIA43-1 | Cys | 3 | 37 | 4 | 82 | 1 | 17 | 0 | 100 |
| TMAOIA44-1 | Cys | 4 | 37 | 4 | 26 | 0 | 73 | 0 | 100 |
| TMAOIA45-1 | Cys | 5 | 37 | 4 | 31 | 3 | 65 | 1 | 100 |
| TMAOIA46-1 | Cys | 6 | 37 | 4 | 77 | 7 | 14 | 2 | 100 |
| TMAOIA47-1 | Cys | 7 | 37 | 4 | 89 | 11 | 0 | 0 | 100 |
| TMAOIA48-1 | Cys | 8 | 37 | 4 | 83 | 17 | 0 | 0 | 100 |
| TMAOIA51-1 | GSH | 5 | 50 | 4 | 0 | 0 | 100 | 0 | 100 |
| TMAOIA53-1 | Cys | 3 | 50 | 4 | 72 | 0 | 28 | 0 | 100 |
| TMAOIA54-1 | Cys | 4 | 50 | 4 | 0 | 0 | 100 | 0 | 100 |
| TMAOIA55-1 | Cys | 5 | 50 | 4 | 0 | 100 | 0 | 0 | 100 |
| TMAOIA56-1 | Cys | 6 | 50 | 4 | 0 | 0 | 0 | 0 | 0 |
| TMAOIA57-1 | Cys | 7 | 50 | 4 | 0 | 0 | 0 | 0 | 0 |
| TMAOIA58-1 | Cys | 8 | 50 | 4 | 0 | 100 | 0 | 0 | 100 |
| TMAOIA61-1 | GSH | 5 | 80 | 4 | 0 | 0 | 0 | 0 | 0 |
| TMAOIA63-1 | Cys | 3 | 80 | 4 | 55 | 3 | 42 | 0 | 100 |
| TMAOIA64-1 | Cys | 4 | 80 | 4 | 11 | 3 | 80 | 6 | 100 |
| TMAOIA65-1 | Cys | 5 | 80 | 4 | 23 | 25 | 39 | 13 | 100 |
| TMAOIA66-1 | Cys | 6 | 80 | 4 | 22 | 63 | 0 | 16 | 100 |
| TMAOIA67-1 | Cys | 7 | 80 | 4 | 0 | 100 | 0 | 0 | 100 |
| TMAOIA68-1 | Cys | 8 | 80 | 4 | 26 | 74 | 0 | 0 | 100 |
| TMAOIA41-2 | GSH | 5 | 37 | 54 | 20 | 1 | 66 | 13 | 100 |
| TMAOIA43-2 | Cys | 3 | 37 | 54 | 66 | 1 | 31 | 3 | 100 |

TABLE 6-continued

| sample | conditions of reaction | | | | relative concentration (%) | | | | |
|---|---|---|---|---|---|---|---|---|---|
| | reducing agent | pH | reaction tem. (° C.) | reaction time (h) | TMAO | TMA | ABEt | AB | Total |
| TMAOIA44-2 | Cys | 4 | 37 | 54 | 2 | 2 | 87 | 8 | 100 |
| TMAOIA45-2 | Cys | 5 | 37 | 54 | 21 | 1 | 64 | 14 | 100 |
| TMAOIA46-2 | Cys | 6 | 37 | 54 | 86 | 0 | 6 | 9 | 100 |
| TMAOIA47-2 | Cys | 7 | 37 | 54 | 99 | 0 | 0 | 1 | 100 |
| TMAOIA48-2 | Cys | 8 | 37 | 54 | 100 | 0 | 0 | 0 | 100 |
| TMAOIA51-2 | GSH | 5 | 50 | 16 | 11 | 0 | 70 | 19 | 100 |
| TMAOIA53-2 | Cys | 3 | 50 | 16 | 47 | 1 | 47 | 5 | 100 |
| TMAOIA54-2 | Cys | 4 | 50 | 16 | 8 | 0 | 83 | 9 | 100 |
| TMAOIA55-2 | Cys | 5 | 50 | 16 | 48 | 0 | 39 | 13 | 100 |
| TMAOIA56-2 | Cys | 6 | 50 | 16 | 86 | 2 | 4 | 9 | 100 |
| TMAOIA57-2 | Cys | 7 | 50 | 16 | 98 | 0 | 0 | 2 | 100 |
| TMAOIA58-2 | Cys | 8 | 50 | 16 | 100 | 0 | 0 | 0 | 100 |
| TMAOIA61-2 | GSH | 5 | 80 | 16 | 40 | 1 | 18 | 41 | 100 |
| TMAOIA63-2 | Cys | 3 | 80 | 16 | 11 | 40 | 37 | 12 | 100 |
| TMAOIA64-2 | Cys | 4 | 80 | 16 | 11 | 4 | 56 | 29 | 100 |
| TMAOIA65-2 | Cys | 5 | 80 | 16 | 4 | 44 | 13 | 40 | 100 |
| TMAOIA66-2 | Cys | 6 | 80 | 16 | 88 | 2 | 0 | 11 | 100 |
| TMAOIA67-2 | Cys | 7 | 80 | 16 | 98 | 0 | 0 | 2 | 100 |
| TMAOIA68-2 | Cys | 8 | 80 | 16 | 100 | 0 | 0 | 0 | 100 |

Figure 17:
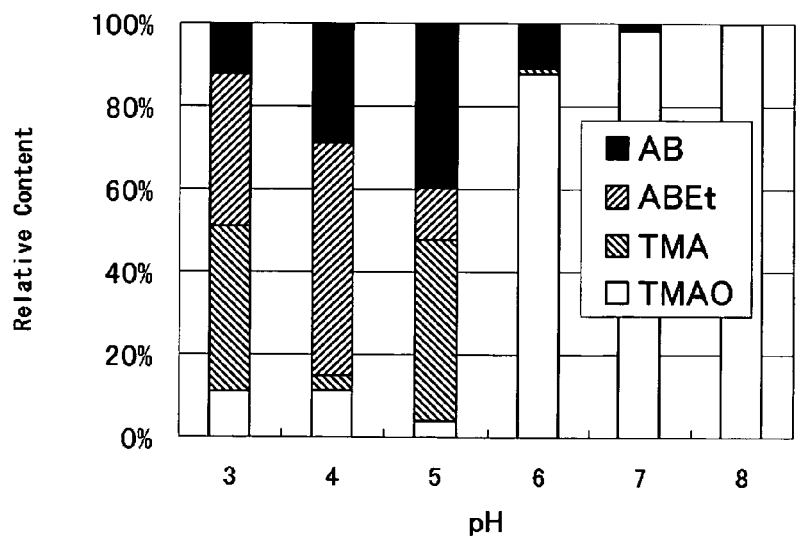
FIG. 17 gives the relative concentration of arsenic compound in various sort of pH after the reaction at 80° C., for 16 hours in the Example 3.

Furthermore, the results calculated on percentage of the relative concentration as to the concentration of the arsenic compound of the table 5 are shown in the table 6. Further, FIG. 17 shows a relative concentration of the arsenic compound at each pHs in the case of at 80° C. of the reaction temperature, 16 hours of the reaction time.

Example 4

Into a 100 μL of the sample mentioned in the example 3 (TMAOIA44; the use of Cysteine as the reducing agent), a 100 μL of 6N HCl was added and reacted under the reaction conditions described in table 7. The reaction formula is as follows.

[Chemical 2]

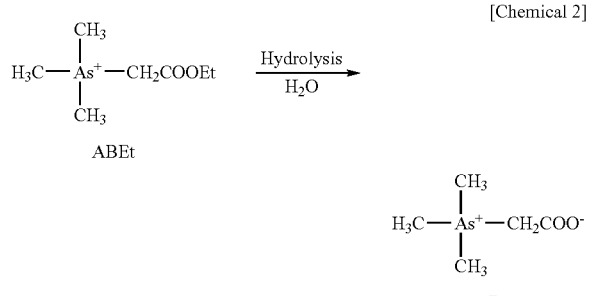

ABEt

AB

The amount of production of the arsenic compounds existing in the mixture after the reaction was analyzed by HPLC-ICP-MS. The results are shown in the table 7. The TMAO was converted to the ABEt in the Example 3. On the other hand, the ABEt was hydrolyzed by adding the hydrochloric acid solution to be converted to AB (arsenobetaine).

TABLE 7

| sample | conditions of reaction | | | concentration of arsenic compound (ng As/mL) | | | |
|---|---|---|---|---|---|---|---|
| | reaction time (h) | reaction temp. (° C.) | pH | TMAO | ABEt | AB | Total |
| TMAOIA44-2 + HCl | 0 | room tem. | 4 | 1.4 | 15.5 | 1.9 | 18.7 |
| TMAOIA44-2 + HCl | 1 | room tem. | 4 | 1.7 | 15.8 | 2.0 | 19.4 |
| TMAOIA44-2 + HCl | 2 | room tem. | 4 | 1.9 | 15.0 | 2.8 | 19.7 |
| TMAOIA44-2 + HCl | 3 | room tem. | 4 | 1.5 | 15.2 | 2.9 | 19.6 |
| TMAOIA44-2 + HCl | 48 | 80° C. | 4 | 0.0 | 0.0 | 24.6 | 24.6 |

Next, the experiment in the case that the methyl compound is produced by alkylating or arylating the harmful compound containing arsenic etc., will be explained (Examples 5-8). Such methyl compound may be also further detoxified according to the above Examples.

Example 5

The methylation of arsenic trioxide is explained in the present Example.

(1) Synthesis of Arsenic Tribromide from Arsenic Trioxide
<Reaction Scheme>

$$As_2O_3 \rightarrow AsBr_3$$

<Experimental Operation>
Arsenic tribromide ($As_2O_3$) (26.5 g), sulfur (6 g) and bromine ($Br_2$) (64 g) were added into a 300 ml flask and were heated gradually (The heat must be carefully carried out because a vapor of $Br_2$ is evaporated and emitted if it is heated rapidly). After about 7 hours, the reaction was continued until a color of a vapor shows no brown color deriving from $Br_2$. The purification was carried out as follows. The distillation purification was carried out by adding a powder of arsenic because a large amount of $Br_2$ might be solved in the produced arsenic tribromide (Yield: >90%). Property: colorless, deliquescent, orthorhombic system columnar crystal, melting point: 31.2° C., boiling point: 221° C., relative density: 3.54 (25° C.). The release of fume came about under an air charged with moisture. The hydrolysis came about by adding a water. Soluble for HCl and $CO_2$. Although as to the toxicity, it is an arsenic trioxide type which is the same as arsenic trichloride, as to the acridity, it is not so strong compared with that of arsenic trichloride.

(2) Synthesis of Arsenic Trichloride from Arsenic Trioxide
<Reaction Scheme>

$$As_2O_3 + 6HCl \rightarrow 2AsCl_3 + 3H_2O$$

<Experimental Operation>

Arsenic trioxide (200 g) was added into 2 l three-neck-flask with stirrer, 700 mL of concentrated hydrochloric acid was added by mixture, 200 ml of concentrated sulfuric acid was dropped gradually. The drop of concentrated sulfuric acid made water which is produced in the above reaction formula be dehydrated, and the reaction proceeded to the right, the produced arsenic trichloride went to the bottom of the flask with the phase separation coming about. After the drop of concentrated sulfuric acid was terminated, it was distilled by heating the flask. Although the distillation starts at 85° C., a lube stock between 90 and 107° C. was collected. A discharge liquor was cooled down, so that it separate off an arsenic trichloride layer (lower layer) and a HCl layer (upper layer). Therefore, arsenic trichloride was separated by the separatory funnel. Yield point: 150 mL, Yield: 89%, Purity: equal to 99% or more.

(3) Synthesis of Trimethyl Arsine from Arsenic Tribromide
<Reaction Scheme>

$$AsBr_3 \rightarrow AsMe_3$$

<Experimental Operation>

To dibutyl ether (200-300 ml) which was entirely dried, magnesium (12.2 g) and methyl iodide (71 g) were added to prepare an ethereal solution of methyl magnesium iodide, and then those which arsenic tribromide (50 g) was solved in ether (100 ml) was added gradually with it being chilled at -20° C. Although a yellow precipitate came about in mid-course, finally it disappeared. After that, an ethereal solution of trimethyl arsine was obtained by distilling it from a bath under air flow of the carbon dioxide gas over the whole (boiling point: 70° C., a liquid)

(4) Synthesis of Trimethyl Arsine from Arsenic Trichloride
<Reaction Scheme>

$$AsCl_3 + 3MeLi \rightarrow AsMe_3 + 3LiCl$$

<Experimental Operation>

Since trimethyl arsine is volatile (boiling point: 52° C.), a protective mask was used. A diethyl ether solution of methyl lithium (500 ml, 0.8 mol/l) and anhydrous dibutyl ether (which is rectified with $CaH_2$, 400 ml) were added into a reactor vessel under argon air flow. Arsenic trichloride solved in dibutyl ether (13.6 ml, 0.16 mol) was added gradually into a reactor. The reaction mixture was reacted for 12 hours under argon gas atmosphere, trimethyl arsine was distilled and was collected in the flask maintained at -35° C. Yield: 99%

Example 6

Next, the methylation of dimethyl arsinic acid will be explained.
<Reaction Scheme>

$$O=AsMe_2(OH) \rightarrow IAsMe_2$$

<Experimental Operation>

(1) Synthesis of Dimethyl Arsenic Iodide from Dimethylarsinic Acid

Dimethylarsinic acid (250 g) and potassium iodide (800 g) were solved in the water (1 L), it was saturated with sulphur dioxide ($SO_2$). To this was added slowly a diluted hydrochloric acid (which was prepared by mixing 500 mL of a concentrated hydrochloric acid with 500 mL of water). The reduction reaction took place rapidly, dimethyl arsenic iodide like yellow oil was separated. The termination of the reaction was determined by a point that sulfur was separated. The separated phase of the oil was dried with calcium chloride and was distilled to obtain a pure dimethyl arsenic iodide (Yield point: 380 g, Yield: 90%). Boiling point: 154-157° C., Melting point: -35° C. (Blue-yellow crystal).

(2) Synthesis of Trimethyl Arsine from Dimethyl Arsenic Iodide
<Reaction Scheme>

$$IAsMe_2 \rightarrow AsMe_3$$

<Experimental Operation>

A suspension of magnesium was prepared with stirring in dried dibutyl ether (100 ml) under the nitrogen atmosphere, to this was added methyl iodide (17.0 g) to prepare the Grignard reagent (Solution A). This cloudy liquid (Solution A) was chilled at -8° C., a solution of dimethyl arsenic iodide (30 g, 129 mmol) solved in dibutyl ether (100 ml) (Solution B) was dropped for 1.5 hours (Solution C). When the operation was terminated, the temperature increased up to -2° C., the solution (Solution C) was separated into two layers. A solution wherein ammonium chloride (30 g) was solved in the water (120 ml) was prepared, after that nitrogen was blew into it to remove oxygen, it was dropped to solution C for 30 min (Solution D). The solution D was distilled under air flow of nitrogen under an atmosphere pressure. A distillate containing trimethyl arsine which was distillated at a boiling point of 55-88° C. (16.5 g, 138 mmol as trimethyl arsine) (solution E) was collected into a Schlenk flask, and was dried with an A4 molecular sieve under nitrogen gas.

Example 7

The conversion of trimethyl arsine into trimethyl arsine oxide will be explained.
<Reaction Scheme>

$$Me_3As \rightarrow Me_3As=O$$

<Experimental Operation>

Under the nitrogen atmosphere, trimethyl arsine (4.5 mmol) was mixed into the dried dibutyl ether (15 ml), to this was added hydrogen peroxide (33%, 0.7 ml, 7 mmol). Under the nitrogen atmosphere, a solution was stirred for 15 min. After the termination of the reaction, the reaction mixture was condensed. The concentrate was heated and dried in vacuum at 50° C. to recrystallize it from 50 ml of diethyl ether—water (1:1 by volume) (6.3 mmol, Yield: 90%).

Example 8

In the Example 8, Synthesis of trimethyl arsine from arsenic trioxide. The reaction formula is as follows.

[Chemical 3]

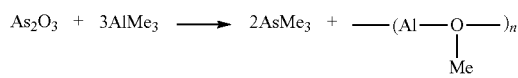

At first, into a 250 mL stainless vessel (2-3 mm of the thickness) a stainless ball having 2-4 mm of diameter is filled up to one fourth full of the vessel. A metal blade for agitation is attached, a hermetic sealing is carried out. A dropping funnel and a reflux tube is attached. A vacuum trap is attached to a reflux cooling tube, it is chilled to −80° C. with an acetone—dry ice to prepare a trap. Further a trap chilled with liquid nitrogen (−196° C.) is attached. A three-way cock is bonded to a water jacket and an inactive gas supplying system. A reactor vessel is charged with inactive gas (Ar). Arsenic trioxide (As$_2$O$_3$) (19.7 g, 0.1 mol) is added into the reactor vessel. Di-n-butyl ether (30 mL) is added. It is stirred with a stirrer for 10 min. The di-n-butyl ether solution (100 mL) of AlMe$_3$ (21.6 g, 0.3 mol) is added to a dropping funnel. Only one fourth full of the di-n-butyl ether solution of AlMe$_3$ is added to the reactor vessel through the dropping funnel. The reactor vessel is heated at 80° C. The exothermic reaction takes place, the temperature of the reaction solution increases to 110-120° C. Between 10 and 15 minutes, the rest of the di-n-butyl ether solution of AlMe$_3$ is added. In this period, the temperature is maintained at 110-120° C. After the drop is terminated, it is allowed for a while to be cooled down up to 80° C., and then under reduced pressure AsMe$_3$ is distilled. The distillation is carried out at 16 Torr, at 50° C. The reaction vessel is filled with an inactive gas (Ar). (Boiling point: 52° C., Yield point: 23.6 g, Yield: 98.5%).

Example 9

In the Examples 1 to 4, while the detoxification of the trimethyl compound has been explained, the detoxification of the monomethyl compound will be explained in the Example.

20 μL of 1 ppm monomethyl arsinic acid (MMA) solution as the metal arsenic and 50 μL of 100 mM glutathione reduced form (GSH) aqueous solution and 270 μL of the predetermined concentration (0.74 μM, 7.4 μM, 74 μM, 740 μM, 7.4 mM) iodoacetic acid (IAA) aqueous solution were mixed. The mixture were reacted in 660 μL of 100 mM phosphoric acid-citrate buffer solution (pH6) at 37° C. for the predetermined time. The molar ratio of iodoacetic acid to the monomethyl arsenic compound is shown by the [IAA]/[As] in the table 8. The mixture after the reaction was diluted by adding the ultrapure water to obtain the hundredfold and analyzed by the HPLC-ICP-MS. The result of this is shown in the table 8. In the table, it is shown that As(III): inorganic arsenic (trivalent state), As(V): inorganic arsenic (pentavalent), MMA: monomethyl arsonic acid, DMA: dimethyl arsinic acid, TMAO: trimethyl arsine oxide, MMAA: monomethyl arsinic acetate, AB: arsenobetaine, the conversion ratio is calculated by the following formula.

The conversion ratio(%)=total concentration of the arsenic compound after the reaction/total concentration of the arsenic compound before the reaction×100

TABLE 8

| No. | molar ratio [IAA]/[As] | reaction time [hr] | As(III) | As(V) | MMA | DMA | TMAO | MMAA | AB | Total | conversion ratio [%] |
|---|---|---|---|---|---|---|---|---|---|---|---|
| 1-1 | 1 | 1 | 0 | 0 | 13 | 0 | 0 | 87 | 0 | 100 | ~100 |
| 1-2 | 1 | 12 | 0 | 0 | 17 | 0 | 0 | 83 | 0 | 100 | ~100 |
| 2-1 | 10 | 1 | 0 | 0 | 0 | 0 | 0 | 100 | 0 | 100 | ~100 |
| 2-2 | 10 | 24 | 0 | 0 | 0 | 0 | 0 | 100 | 0 | 100 | ~100 |
| 2-3 | 10 | 100 | 0 | 0 | 0 | 0 | 0 | 100 | 0 | 100 | ~100 |
| 3-1 | 100 | 1 | 0 | 0 | 16 | 0 | 0 | 84 | 0 | 100 | ~100 |
| 3-2 | 100 | 100 | 0 | 0 | 0 | 0 | 0 | 100 | 0 | 100 | ~100 |
| 4-1 | 1,000 | 1 | 29 | 0 | 12 | 0 | 0 | 60 | 0 | 100 | ~100 |
| 4-2 | 1,000 | 12 | 0 | 0 | 13 | 0 | 0 | 87 | 0 | 100 | ~100 |
| 4-3 | 1,000 | 24 | 0 | 0 | 0 | 0 | 0 | 100 | 0 | 100 | ~100 |
| 5-1 | 10,000 | 1 | 30 | 0 | 15 | 0 | 0 | 55 | 0 | 100 | ~100 |
| 5-2 | 10,000 | 12 | 0 | 0 | 20 | 0 | 0 | 80 | 0 | 100 | ~100 |
| 5-3 | 10,000 | 24 | 0 | 0 | 51 | 0 | 0 | 49 | 0 | 100 | ~100 |
| 5-4 | 10,000 | 100 | 0 | 0 | 29 | 0 | 0 | 71 | 0 | 100 | ~100 |

A peak which attributes to MMAA was confirmed in the Example. Monomethyl arsonic acid was methylated (carboxymethylation) to be converted to more harmless compound. The detoxification reaction of monomethyl arsenic is as follows.

[Chemical 4]

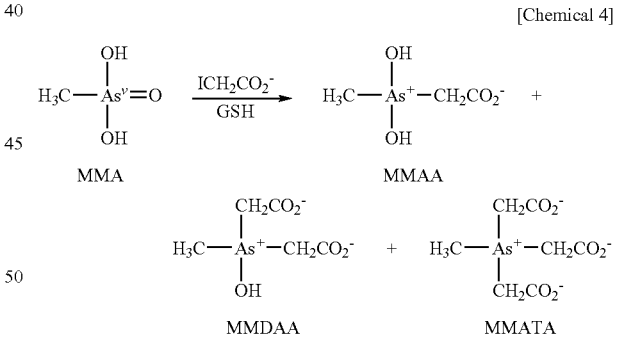

Monomethyl arsinic diacetate (MMDAA), monomethyl arsinic triacetate (MMTAA) may be obtained as the product other than monomethyl arsinic acetate (MMAA) by the detoxification of monomethyl arsenic.

Example 10

The detoxification of the dimethyl compound will be explained in the same manner as in Example 9, except that dimethyl arsinic acid (DMA) was used instead of MMA solution. The result of this is shown in the table 9.

TABLE 9

| No. | molar ratio [IAA]/[As] | reaction time [hr] | As(III) | As(V) | DMA | TMAO | UN13 | UN14 | AB | UN35 | Total | conversion ratio [%] |
|---|---|---|---|---|---|---|---|---|---|---|---|---|
| 6-1 | 1 | 1 | 0 | 0 | 100 | 0 | 0 | 0 | 0 | 0 | 100 | ~100 |
| 6-2 | 1 | 12 | 0 | 0 | 100 | 0 | 0 | 0 | 0 | 0 | 100 | ~100 |
| 6-3 | 1 | 24 | 0 | 0 | 100 | 0 | 0 | 0 | 0 | 0 | 100 | ~100 |
| 6-4 | 1 | 100 | 0 | 0 | 100 | 0 | 0 | 0 | 0 | 0 | 100 | ~100 |
| 7-1 | 10 | 1 | 0 | 0 | 59 | 0 | 41 | 0 | 0 | 0 | 100 | ~100 |
| 7-2 | 10 | 12 | 0 | 0 | 100 | 0 | 0 | 0 | 0 | 0 | 100 | ~100 |
| 7-3 | 10 | 24 | 0 | 0 | 0 | 0 | 0 | 0 | 0 | 100 | 100 | 70 |
| 7-4 | 10 | 100 | 0 | 0 | 0 | 0 | 0 | 0 | 0 | 100 | 100 | ~100 |
| 8-1 | 100 | 1 | 0 | 0 | 64 | 0 | 36 | 0 | 0 | 0 | 100 | ~100 |
| 8-2 | 100 | 12 | 0 | 0 | 100 | 0 | 0 | 0 | 0 | 0 | 100 | ~100 |
| 8-3 | 100 | 24 | 0 | 0 | 100 | 0 | 0 | 0 | 0 | 0 | 100 | ~100 |
| 9-1 | 1,000 | 1 | 0 | 0 | 66 | 0 | 34 | 0 | 0 | 0 | 100 | ~100 |
| 9-2 | 1,000 | 12 | 0 | 0 | 100 | 0 | 0 | 0 | 0 | 0 | 100 | ~100 |
| 9-3 | 1,000 | 24 | 0 | 0 | 100 | 0 | 0 | 0 | 0 | 0 | 100 | ~100 |
| 9-4 | 1,000 | 100 | 0 | 0 | 100 | 0 | 0 | 0 | 0 | 0 | 100 | |
| 10-1 | 10,000 | 1 | 0 | 0 | 65 | 0 | 0 | 35 | 0 | 0 | 100 | ~100 |
| 10-2 | 10,000 | 12 | 0 | 0 | 62 | 0 | 0 | 38 | 0 | 0 | 100 | ~100 |
| 10-3 | 10,000 | 24 | 0 | 0 | 68 | 0 | 0 | 32 | 0 | 0 | 100 | ~100 |
| 10-4 | 10,000 | 100 | 0 | 0 | 42 | 0 | 0 | 58 | 0 | 0 | 100 | ~100 |

A peak (UN13) which attributes to dimethyl arsinic acetate (DMAA) and a peak (UN14) which attributes to dimethyl arsinic diacetate (DMADAA) were confirmed in the Example. Dimethyl arsinic acid was methylated (carboxymethylation) to be converted to more harmless compound. The detoxification reaction of dimethyl arsenic is as follows.

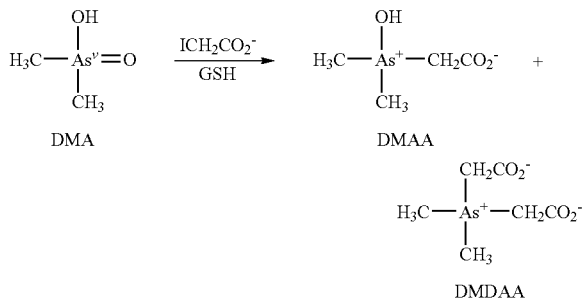

Example 11

The detoxification of the trimethyl compound will be explained in the same manner as in Example 9, except that trimethyl arsine oxide (TMAO) was used instead of MMA solution. The result of this is shown in the table 10.

TABLE 10

| No. | molar ratio [IAA]/[As] | reaction time [hr] | As(III) | As(V) | TMAO | UN13 | UN14 | AB | UN35 | Total | conversion ratio [%] |
|---|---|---|---|---|---|---|---|---|---|---|---|
| 11-1 | 100 | 1 | 0 | 0 | 0 | 0 | 0 | 100 | 0 | 100 | 100 |
| 11-2 | 100 | 12 | 0 | 0 | 0 | 0 | 0 | 100 | 0 | 100 | 80 |
| 11-3 | 100 | 24 | 0 | 0 | 0 | 0 | 0 | 100 | 0 | 100 | ~100 |
| 11-4 | 100 | 100 | 0 | 0 | 0 | 0 | 0 | 100 | 0 | 100 | 100 |
| 12-1 | 1,000 | 1 | 0 | 0 | 0 | 0 | 0 | 100 | 0 | 100 | ~100 |
| 12-2 | 1,000 | 12 | 0 | 0 | 0 | 0 | 0 | 100 | 0 | 100 | ~100 |
| 12-3 | 1,000 | 24 | 0 | 0 | 0 | 0 | 0 | 100 | 0 | 100 | ~100 |
| 12-4 | 1,000 | 100 | 0 | 0 | 0 | 0 | 0 | 100 | 0 | 100 | ~100 |
| 13-1 | 10,000 | 1 | 0 | 0 | 0 | 0 | 0 | 100 | 0 | 100 | ~100 |
| 13-2 | 10,000 | 12 | 0 | 0 | 0 | 0 | 0 | 100 | 0 | 100 | ~100 |
| 13-3 | 10,000 | 24 | 0 | 0 | 0 | 0 | 0 | 100 | 0 | 100 | ~100 |

A peak which attributes to AB (arsenobetaine; trimethyl arsinic acetate) was confirmed in the Example. Trimethyl arsine oxide (TMAO) was methylated (carboxymethylation) to be converted to more harmless compound. The detoxification reaction of trimethyl arsenic is as follows.

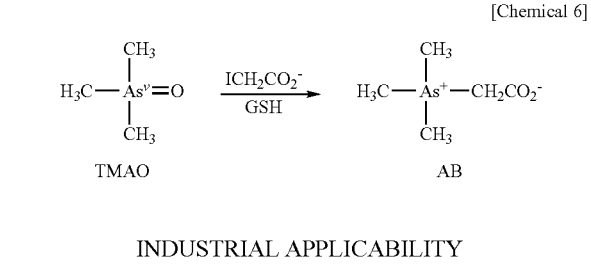

INDUSTRIAL APPLICABILITY

The methods of detoxifying the methyl compound according to the present inventions make a significant contribution in the broad fields of treatments of the industrial waste etc., and environmental protections concerning a polluted mud or a soil, since the harmless compound obtained by converting the methyl compounds to more harmless compound is extremely stable and safe.

The invention claimed is:

1. A method of detoxifying a methyl compound, comprising: reacting in vitro within an aqueous solvent, an organic halogenated compound with a methyl compound in the presence of a reducing agent, wherein the reducing agent is capable of reducing at least one selected from the group consisting of arsenic, antimony and selenium, and the reducing agent is at least one selected from the group consisting of reduced glutathione (GSH), oxidized glutathione, cysteine, S-adenosyl cysteine, sulforaphane and mercaptoalcohol, wherein the methyl compound comprises arsenic, and wherein in the reaction between the organic halogenated compound with the methyl compound, the methyl compound is methylated, thereby converting the methyl compound into trimethylarsineoxide, and further converting trimethylarsineoxide into arsenobetaine in the presence of the reducing agent that is at least one selected from the group consisting of reduced glutathione (GSH), oxidized glutathione, cysteine, S-adenosyl cysteine, sulforaphane and mercaptoalcohol.

2. A method of detoxifying a methyl compound according to claim 1, wherein the methyl compound is at least one selected from the group consisting of monomethyl compound, dimethyl compound and trimethyl compound.

3. A method of detoxifying a methyl compound according to claim 1, wherein the organic halogenated compound is alkyl halide.

4. A method of detoxifying a methyl compound according to claim 3, wherein the alkyl halide is methyl halide.

5. A method of detoxifying a methyl compound according to claim 4, wherein the methyl halide is at least one selected from the group consisting of methyl iodide, methyl bromide and methyl chloride.

6. A method of detoxifying a methyl compound according to claim 3, wherein the alkyl halide is halogenated acetic acid, halogenated alcohol or halogenated ester.

7. A method of detoxifying a methyl compound according to claim 6, wherein the halogenated acetic acid is at least one selected from the group consisting of chloroacetic acid, bromoacetic acid, iodoacetic acid, chloropropionic acid, bromopropionic acid and iodopropionic acid.

8. A method of detoxifying a methyl compound according to claim 6, wherein the halogenated alcohol is at least one selected from the group consisting of chloroethanol, bromoethanol and iodoethanol.

9. A method of detoxifying a methyl compound according to claim 1, wherein a pH of the reaction solution is in the range of 3-10.

10. A method of detoxifying a methyl compound according to claim 1, wherein the methyl compound is originally from a contaminant, a waste product, industrial products, hot spring water, a chemical reagent, a chemical weapon, a secondary product of a mine or a smeltery, industrial goods or a natural environment.

11. A method of detoxifying a methyl compound according to claim 1, wherein the methylation is attained by increasing the oxidation number of a valence of arsenic.

12. A method of detoxifying a methyl compound according to claim 1, wherein at least one bond of arsenic is methylated.

13. A method of detoxifying a methyl compound according to claim 1, wherein the methyl compound is halogenated, and then the halogenated methyl compound is methylated by the Grignard reaction.

14. A method of detoxifying a methyl compound according to claim 1, wherein the arsenic is at least one selected from the group consisting of arsenious acid, arsenic pentoxide, arsenic trichloride, arsenic pentachloride, arsenic sulfide compound, cyano arsenic compound and chloro arsenic compound, wherein each of arsenious acid, arsenic pentoxide, arsenic trichloride, arsenic pentachloride, arsenic sulfide compound, cyano arsenic compound and chloro arsenic compound is methylated.

* * * * *